United States Patent
Abu-Baker et al.

(10) Patent No.: US 10,668,038 B2
(45) Date of Patent: **\*Jun. 2, 2020**

(54) EMULSION AND EMULSION PRECONCENTRATE COMPOSITIONS COMPRISING OMEGA-3 FATTY ACIDS AND USES THEREOF ARE DISCLOSED

(71) Applicant: MOCHIDA PHARMACEUTICAL CO., LTD., Tokyo (JP)

(72) Inventors: Omar Abdelfattah Abu-Baker, King of Prussia, PA (US); Donald MacKenzie, Collegeville, PA (US); Rennan Pan, Collegeville, PA (US)

(73) Assignee: MOCHIDA PHARMACEUTICAL CO., LTD., Tokyo (JP)

( * ) Notice: Subject to any disclaimer, the term of this patent is extended or adjusted under 35 U.S.C. 154(b) by 17 days.

This patent is subject to a terminal disclaimer.

(21) Appl. No.: 15/631,104

(22) Filed: Jun. 23, 2017

(65) Prior Publication Data

US 2017/0304249 A1    Oct. 26, 2017

Related U.S. Application Data

(63) Continuation of application No. 13/502,214, filed as application No. PCT/US2010/052840 on Oct. 15, 2010, now Pat. No. 9,717,703.

(60) Provisional application No. 61/267,697, filed on Dec. 8, 2009, provisional application No. 61/252,310, filed on Oct. 16, 2009.

(51) Int. Cl.
| | |
|---|---|
| *A61K 31/202* | (2006.01) |
| *A61K 9/08* | (2006.01) |
| *A61K 9/107* | (2006.01) |
| *A61K 9/12* | (2006.01) |
| *A61K 31/20* | (2006.01) |
| *A61K 31/225* | (2006.01) |
| *A61K 47/14* | (2017.01) |
| *A61K 47/34* | (2017.01) |
| *A61K 47/44* | (2017.01) |
| *A23D 7/01* | (2006.01) |
| *A23D 7/015* | (2006.01) |
| *A23L 33/12* | (2016.01) |
| *A61K 45/06* | (2006.01) |
| *A61K 9/14* | (2006.01) |

(52) U.S. Cl.
CPC ........... *A61K 31/202* (2013.01); *A23D 7/011* (2013.01); *A23D 7/015* (2013.01); *A23L 33/12* (2016.08); *A61K 9/107* (2013.01); *A61K 9/1075* (2013.01); *A61K 9/14* (2013.01); *A61K 31/20* (2013.01); *A61K 31/225* (2013.01); *A61K 45/06* (2013.01); *A61K 47/14* (2013.01); *A61K 47/34* (2013.01); *A61K 47/44* (2013.01); *A23V 2002/00* (2013.01); *A61K 9/08* (2013.01)

(58) Field of Classification Search
None
See application file for complete search history.

(56) References Cited

U.S. PATENT DOCUMENTS

| | | |
|---|---|---|
| 4,096,258 A | 6/1978 | Hanson |
| 4,192,898 A | 3/1980 | Hanson |
| 4,665,098 A | 5/1987 | Gibbs et al. |
| 5,385,737 A | 1/1995 | Shiqeno et al. |
| 5,407,683 A | 4/1995 | Shively |
| 5,478,508 A | 12/1995 | Suzuki et al. |
| 5,502,077 A | 3/1996 | Breivik et al. |
| 5,532,002 A | 7/1996 | Story |
| 5,567,592 A | 10/1996 | Benet et al. |
| 5,567,730 A | 10/1996 | Miyashita et al. |
| 5,882,680 A | 3/1999 | Suzuki et al. |
| 5,885,629 A | 3/1999 | Ford |
| 5,965,160 A | 10/1999 | Benita et al. |
| 6,103,770 A | 8/2000 | Trouve |
| 6,121,313 A | 9/2000 | Gao et al. |
| 6,231,887 B1 | 5/2001 | Gao et al. |
| 6,284,268 B1 | 9/2001 | Mishra et al. |
| 6,531,139 B1 | 3/2003 | Gao et al. |
| 6,979,456 B1 | 12/2005 | Parikh et al. |
| 7,182,950 B2 | 2/2007 | Garti et al. |
| 7,687,066 B2 | 3/2010 | Fujino et al. |
| 7,736,666 B2 | 6/2010 | Holmberg et al. |
| 8,158,134 B1 | 4/2012 | Supersaxo et al. |
| 8,168,225 B2 | 5/2012 | Casana-Giner et al. |
| 8,198,324 B2 | 6/2012 | Fortin |
| 8,222,295 B2 | 7/2012 | Fortin |
| 8,337,931 B2 | 12/2012 | Bromley |
| 8,440,726 B2 | 5/2013 | Ohkawa |
| 8,513,311 B2 | 8/2013 | Sagalowicz et al. |
| 8,765,661 B2 | 7/2014 | Bromley |
| 9,370,493 B2 | 6/2016 | Klaveness et al. |

(Continued)

FOREIGN PATENT DOCUMENTS

| | | |
|---|---|---|
| EP | 0184942 A2 | 6/1986 |
| EP | 0292050A 1 | 11/1988 |

(Continued)

OTHER PUBLICATIONS

Amidon et al, Theoretical and experimental studies of transport of micelle-solubilized solutes, Journal of Pharmaceutical Sciences, vol. 71, Issue 1 (Jan. 1982) 77-84.

Anderberg et al, Epithelial transport of drugs in cell culture. VII: Effects of pharmaceutical surfactant excipients and bile acids on transepithelial permeability in monolayers of human intestinal epithelial (Caco-2) cells, J Pharm Scie, vol. 81, No. 9, (Sep. 1992) 879-887.

Aungst, Novel formulation strategies for improving oral bioavailability of drugs with poor membrane permeation or presystemic metabolism, J Pharm Sci, vol. 82, No. 10 (Oct. 1993) 979-985.

Bogman et al, The role of surfactants in the reversal of active transport mediated by multidrug resistance proteins, J Pharm Scie, vol. 92, No. 6 (Jun. 2003) 1250-1261.

(Continued)

*Primary Examiner* — Bethany P Barham
*Assistant Examiner* — Barbara S Frazier
(74) *Attorney, Agent, or Firm* — Birch, Stewart, Kolasch & Birch, LLP

(57) ABSTRACT

Novel compositions comprising omega-3 fatty acids and uses thereof are disclosed.

15 Claims, No Drawings

(56) References Cited

U.S. PATENT DOCUMENTS

| | | | |
|---|---|---|---|
| 9,452,150 | B2 | 9/2016 | Ueshima et al. |
| 9,532,963 | B2 | 1/2017 | Hustvedt et al. |
| 2002/0102301 | A1 | 8/2002 | Schwarz |
| 2002/0119198 | A1 | 8/2002 | Gao et al. |
| 2003/0072798 | A1 | 4/2003 | Schwarz |
| 2003/0105141 | A1 | 6/2003 | Gao et al. |
| 2003/0129219 | A1 | 7/2003 | Hong et al. |
| 2003/0161846 | A1 | 8/2003 | Holmberg et al. |
| 2003/0235595 | A1 | 12/2003 | Chen et al. |
| 2003/0235596 | A1 | 12/2003 | Gao et al. |
| 2004/0018248 | A1 | 1/2004 | Bendich |
| 2004/0052824 | A1 | 3/2004 | Abou Chacra-Vernet et al. |
| 2004/0081670 | A1 | 4/2004 | Holman |
| 2004/0121000 | A1 | 6/2004 | Bowe et al. |
| 2004/0185068 | A1 | 9/2004 | Yu et al. |
| 2004/0191284 | A1 | 9/2004 | Yu et al. |
| 2005/0037073 | A1 | 2/2005 | Schwarz |
| 2005/0106233 | A1 | 5/2005 | Andersen et al. |
| 2005/0187292 | A1 | 8/2005 | Aoki et al. |
| 2005/0196370 | A1 | 9/2005 | Yu et al. |
| 2005/0209345 | A1 | 9/2005 | Charman |
| 2005/0238675 | A1 | 10/2005 | Lu et al. |
| 2006/0034815 | A1 | 2/2006 | Guzman et al. |
| 2006/0051462 | A1 | 3/2006 | Wand |
| 2006/0083824 | A1 | 4/2006 | Manning et al. |
| 2006/0088574 | A1 | 4/2006 | Manning et al. |
| 2006/0165735 | A1 | 7/2006 | Abril et al. |
| 2006/0182771 | A1 | 8/2006 | Dor et al. |
| 2006/0251685 | A1 | 11/2006 | Yu et al. |
| 2006/0292217 | A1 | 12/2006 | Schmidt et al. |
| 2007/0031538 | A1 | 2/2007 | Konuklar |
| 2007/0148309 | A1 | 6/2007 | Behman |
| 2007/0259097 | A1 | 11/2007 | Andersen et al. |
| 2008/0038335 | A1 | 2/2008 | Huang |
| 2008/0193519 | A1 | 8/2008 | Pachot et al. |
| 2008/0311207 | A1 | 12/2008 | Varshney et al. |
| 2009/0012157 | A1 | 1/2009 | Rongen et al. |
| 2010/0196456 | A1 | 8/2010 | Strasser |
| 2010/0240753 | A1 | 9/2010 | Ng et al. |
| 2012/0196934 | A1 | 8/2012 | Hustvedt et al. |

FOREIGN PATENT DOCUMENTS

| | | |
|---|---|---|
| EP | 1548093 A 1 | 6/2005 |
| EP | 1616560 A 1 | 1/2006 |
| JP | 63101320 | 5/1988 |
| JP | 2001-152179 A | 6/2001 |
| JP | 2004-514684 A | 5/2004 |
| JP | 2007-523049 A | 8/2007 |
| JP | 2008-509154 A | 3/2008 |
| JP | 2008-1 78341 A1 | 8/2008 |
| JP | 2010-155799 A | 7/2010 |
| KR | 2002042218 A | 6/2002 |
| KR | 2008022739 A | 3/2008 |
| WO | WO91-018613 | 12/1991 |
| WO | WO93-002665 | 2/1993 |
| WO | WO 94/01001 | 1/1994 |
| WO | WO 99/29316 | 6/1999 |
| WO | WO99-029399 | 6/1999 |
| WO | WO99-056727 | 11/1999 |
| WO | WO01-028519 | 4/2001 |
| WO | WO 2002/17906 | 3/2002 |
| WO | WO03-105607 | 12/2003 |
| WO | WO05-03 7250 | 4/2005 |
| WO | WO05-037251 | 4/2005 |
| WO | WO 2006/096806 | 9/2006 |
| WO | WO07-047237 | 4/2007 |
| WO | WO 2008/30949 | 3/2008 |
| WO | WO 2008/101344 | 8/2008 |
| WO | WO08-113177 | 9/2008 |
| WO | WO 2009/117152 | 9/2009 |
| WO | WO 2010/103404 | 9/2010 |

OTHER PUBLICATIONS

Brunton et al, Differentiating prescription omega-3-acid ethyl esters (P-OM3) from dietary supplement omega-3 fatty acids, Current Medical Research and Opinion, vol. 23, No. 5 (2007) 1139-1145.

Bryhn et al, The bioavailability and pharmacodynamics of different concentrations of omega-3 acid ethyl esters, Prostaglandins, Leukotrienes and Essential Fatty Acids 75 (2006) 19-24.

Chen, Lipid excipients and delivery systems for pharmaceutical development: a regulatory perspective, Advanced Drug Delivery Reviews 60 (2008) 768-777.

Chervinsky et al, Cremophor-EL enhances taxol efficacy in a multi-drug resistant C1300 neuroblastoma cell line, Anticancer Research 13 (1993) 93-96.

Cornaire et al, Impact of excipients on the absorption of P-glycoprotein substrates in vitro and in vivo, International Journal of Pharmaceutics 278 (2004) 119-131.

Daher, Effect of surfactant, Tween 80, on the formation and secretion of chylomicrons in the rat, Food Chem Toxicol, 41(4) (Apr. 2003) 575-582.

Donegan et al, Effect of a dietary nonionic surfactant on small intestinal nutrient transport, Dig Dis Sci, 44(7) (1999) 1423-1427.

Gao et al, Application of a mixture experimental design in the optimization of a self-emulsifying formulation with a high drug load, Pharmaceutical Development and Technology vol. 9, No. 3 (2004) 301-309.

Garaiova et al, A randomized cross-over trial in healthy adults indicating improved absorption of omega-3 fatty acids by pre-emulsification, Nutrition Journal 6:4 (2007) 9 pages.

Gibson, Lipid-Based Excipients for Oral Drug Delivery, 33-61. (book chapter from Oral lipid-based formulations : enhancing the bioavailability of poorly water-soluable drugs, David J. Hauss, Ed., New York : Informa Healthcare, c2007).

Gursoy et al, Self-emulsifying drug delivery systems (SEDDS) for improved oral delivery of lipophilic drugs, Biomedicine & Pharmacotherapy 58 (2004) 173-182.

KR2002042218A Derwent abstract DWPX—(C) Thomson Reuters AN-2003-718438/68; PatBase family & abstract; Google Translate machine translation part (Mar. 13, 2017).

KR2008022739A Derwent abstract DWPX—(C) Thomson Reuters AN-2008-M96483/76; Chem abstract AN 2008:430280 HCAPLUS; PatBase family & abstract; Google Translate machine translation part (Mar. 13, 2017).

WO01-28519 Derwent abstract DWPX—(C) Thomson Reuters AN-2001-417530/44; PatBase family & abstract.

JP H6-298642 A—English abstract and partial translation.
JP 2008-178341 A 1—English abstract and partial translation.
JP 2010-155799 A—English abstract and partial translation.
EP2488022—Third Party Observations Sep. 9, 2015.
EP2488022—EPO Office Action dated Jan. 27, 2016.
JP2001-152179A—PatBaseExpress abstracted information.
Japanese Patent Application No. 2012-534391—Third Party Presentation of Information Dec. 7, 2013.
Notification of Reasons for Refusal dated Sep. 4, 2018, in Japanese Patent Application No. 2017-201136, with partial English translation (translation omitted; list of cited documents only).

EMULSION AND EMULSION PRECONCENTRATE COMPOSITIONS COMPRISING OMEGA-3 FATTY ACIDS AND USES THEREOF ARE DISCLOSED

FIELD OF THE INVENTION

The present invention relates to improved formulations of omega-3 fatty acids. More particularly, the present invention relates to improved emulsion or emulsion pre-concentrate formulations of omega-3 fatty acids.

BACKGROUND OF INVENTION

Various omega-3 fatty acids and uses thereof, including in pharmaceutical, nutritional or dietary supplement products, are known in the art. See, e.g., U.S. Pat. Nos. 5,502,077, 5,656,667 and 5,698,594.

One pharmaceutical product is known as LOVAZA® (active name "omega-3-acid ethyl esters"), a lipid-regulating agent approved by the U.S. Food and Drug Administration as an adjunct to diet to reduce triglyceride levels in adult patients with very high (>500 mg/dL) triglyceride levels, at a dose of 4 g per day (either as a single 4-g dose (4 capsules) or as two 2-g doses (2 capsules given twice daily)).

LOVAZA® is marketed as a liquid-filled gel capsule for oral administration. Each 1 gram capsule of LOVAZA® contains at least 900 mg of ethyl esters of omega-3 fatty acids. These are predominantly a combination of ethyl esters of EPA (approximately 465 mg) and DHA (approximately 375 mg). LOVAZA® capsules also contain the inactive ingredients: 4 mg α tocopherol (in a carrier of vegetable oils including soybean oil), and gelatin, glycerol, and purified water (components of the capsule shell).

The Third Report of the National Cholesterol Education Program Expert Panel on Detection, Evaluation, and Treatment of High Blood Cholesterol in Adults, NIH Publication No. 02-5215 (September 2002) (also known as the "NCEP ATP III"), Guidelines classify triglycerides as normal (<150 mg/dL), borderline high (150-199 mg/dL), high (200-499 mg/dL), and as very high (≥500 mg/dL). While LOVAZA® has demonstrated efficacy in reducing triglycerides in the very high triglyceride population, for many patients, their triglycerides remain above normal levels.

It would be advantageous to increase the therapeutic effect of omega-3 fatty acid compositions such as LOVAZA®, e.g. to provide improved methods of treatment such as reducing elevated triglycerides. One approach to increasing the therapeutic effect of orally-administered drugs is to increase the exposure or absorption of the drug after oral administration. It may therefore be advantageous to increase the exposure of omega-3 fatty acids following oral administration. It would be particularly advantageous if an increased therapeutic effect could be provided without increasing the burden of administration, such as pill or capsule burden, e.g., maintaining or even reducing the dosage amount and/or frequency, e.g. the number and/or size of capsules. Reducing the administration burden may, for example, allow for easier administration, improve patient compliance, reduce side effects such as eructation, reduce caloric intake, reduce exposure to any undesired components which may be present in some omega-3 products, and/or reduce cost of therapy.

The literature includes various references which disclose studies involving fish oil and/or omega-3 fatty acid compositions, which in some instances may be emulsified or emulsifiable compositions. See, e.g., Garaiova et al. Nutrition Journal 2007, 6:4 (http://www.nutritionj.com/contents/6/1/4); Raatz et al. Jnl of the American Dietetic Association June 2009 Vol 109 No.6 1076-1081; Mishra et al. U.S. Pat. No. 6,284,268, issued Sep. 4, 2001; WO2008/101344; and Bryhn, M. et al., Prostaglandins, Leukotrienes and Essential Fatty Acids 75:19-24 2006.

SUMMARY OF THE INVENTION

The present invention relates to novel emulsion compositions and emulsion pre-concentrate compositions.

In one aspect, the invention relates to an emulsion composition comprising: an aqueous phase comprising an aqueous liquid; an oil phase comprising an omega-3 fatty acid oil; and a surfactant; wherein the emulsion has a median particle size of from about 100 nm to about 3 μm.

In another aspect, the invention relates to an emulsion composition comprising: an aqueous liquid providing about 65 to about 80 wt % water; about 15 to about 30 wt % of an omega-3 fatty acid oil; and about 5 to about 10 wt % of a surfactant; based on the total weight of the emulsion composition.

In another aspect, the invention relates to an emulsion pre-concentrate composition comprising: an omega-3 fatty acid oil and a surfactant; wherein with contact with an aqueous liquid, the pre-concentrate is capable of forming an emulsion having a median particle size of from about 100 nm to about 3 μm.

Another aspect of the invention relates to an emulsion pre-concentrate composition comprising: from about 60 to about 85 wt % of an omega-3 fatty acid oil; and from about 15 to about 40 wt % of a surfactant; based on the total weight of the omega-3 fatty acid oil and the surfactant in the composition.

In another aspect, the invention relates to an emulsion formed by contacting an emulsion pre-concentrate composition of the invention with an aqueous liquid.

In another aspect, the invention relates to oral dosage forms such as pharmaceutical, nutritional or dietary supplement products, comprising an emulsion or emulsion pre-concentrate composition of the invention.

The invention also relates to use of an emulsion or emulsion pre-concentrate composition of the invention, for the manufacture of a pharmaceutical, nutritional or dietary supplement product suitable for treatment of any of the diseases, conditions or the like for which the omega 3 fatty acid oil may be used.

The invention also relates to a method of treatment comprising administering an emulsion or an emulsion pre-concentrate composition of the invention to a subject in need thereof, for treatment of any of the diseases, conditions or the like for which the omega 3 fatty acid oil may be used.

In other aspects, the invention relates to a method of increasing oral absorption of an omega-3 fatty acid in a subject in need of treatment with an omega-3 fatty acid, comprising orally administering an emulsion or emulsion pre-concentrate composition of the invention to the subject, wherein the oral absorption is increased compared to the oral absorption after orally administering the omega-3 fatty acid oil.

Other aspects of the invention will be understood in light of this disclosure.

In pre-clinical studies, emulsion and emulsion pre-concentrate compositions of the invention comprising LOVAZA® omega-3 acid ethyl esters, especially those having or providing a median emulsion particle size of from about 100 nm to about 3 μm, have been found to improve the exposure or absorption of the major constituent omega-3 fatty acids following oral administration.

The emulsion and/or emulsion pre-concentrate compositions of the invention may:

increase oral absorption (exposure), oral bioavailability, and/or oral efficacy of one or more of the constituent omega-3 fatty acids of the omega-3 fatty acid oil, relative to the omega-3 fatty acid oil;

provide improved methods of treatment, e.g., treating elevated triglycerides such as reducing elevated triglycerides (e.g., triglyceride levels of >500 mg/dL, or ≥200 mg/dL, or ≥150 mg/dL); and/or enable reduction of dosage levels and/or frequency of the omega-3 fatty acid oil required to achieve effective therapy (e.g., reduce the number and/or size of capsules).

DETAILED DESCRIPTION OF THE INVENTION

Unless otherwise stated or the context requires otherwise:

as used herein in reference to a component of a composition, "a", "an" and "the" include one or more of the components (e.g. "a surfactant" includes one or more surfactants, etc.);

as used herein in reference to a value or range of values, "about" includes the expressly stated value (e.g., "about 100 nm to about 3 μm" includes specifically the range 100 to 3 μm, etc.);

embodiments which comprise stated features may also consist essentially of or consist of those features (e.g. a composition which comprises stated components may also consist essentially of or consist of those components);

the word "comprise", and variations such as "comprises" and "comprising", will be understood to imply the inclusion of a stated integer or step or group of integers but not to the exclusion of any other integer or step or group of integers or steps;

the present invention covers all combinations of particular and preferred groups described herein, for example, a "mixture" of stated components includes mixtures between groups of components and/or among a particular component group (e.g., a mixture of acids, glyceride esters, and alcohol esters encompasses: 1) a mixture of acids; 2) a mixture of acids, glyceride esters, and alcohol esters; etc.).

An emulsion of the invention refers in its conventional sense to a dispersion comprising an aqueous phase and an oil phase. The aqueous phase comprises a medium (preferably a liquid medium) comprising water, including e.g., water per se or other aqueous liquid. The oil phase comprises at least one hydrophobic (lipophilic) organic component (e.g., an omega-3 fatty acid oil).

Emulsions of the invention are oil-in-water (o/w) emulsions, wherein the oil phase comprises an omega-3 fatty acid oil and is dispersed in the aqueous phase, such that the oil phase can be described in the conventional sense as "particulate" or "droplet". However, the emulsion may exhibit to a minor extent features of water-in-oil (w/o) emulsions or other dispersions. Thus the emulsions of the invention may be described as substantially oil-in-water emulsions.

In preferred embodiments, the dispersed phase has a median particle size in the range of from about 100 nm to about 3 μm (including e.g., about 100 nm to about 1 μm, e.g. about 100 nm to about 300 nm). "Median particle size" as used herein refers to the $50^{th}$ percentile of the cumulative size distribution. In some embodiments, the emulsion has an x90 particle size (i.e., $90^{th}$ percentile of the cumulative size distribution) of about 5 μm or less, e.g. about 1.5 μm or less.

In some embodiments, the dispersed phase has both the foregoing median and x90 particle size. Particle sizes are determined as described in the Experimental Section hereinbelow.

In some embodiments, an emulsion of the invention exhibits one or more of the following properties:

a) it is thermodynamically stable, i.e. it remains stable at ambient temperatures (20-30° C., especially 25° C.), e.g. without optically observable separation or substantial formation of larger particle sizes or precipitation, over prolonged periods of time. Preferred emulsions remain stable at ambient temperatures over a period of at least 3 hours, more preferably at least 6 hours, most preferably at least 24 hours; and/or b) it is readily or spontaneously formed with minimal agitation and mixing.

As used herein, an "emulsion pre-concentrate" is a system which, on contact with water (e.g. addition to or mixing with water or an aqueous liquid) is capable of forming an emulsion. An emulsion formed from a pre-concentrate of the invention preferably forms spontaneously or substantially spontaneously when the emulsion pre-concentrate is brought into contact with water; i.e. substantial energy such as heating or use of high shear equipment or other substantial agitation is not required to form the emulsion. For example, the emulsion may form after oral administration of the pre-concentrate under conditions existing in the stomach. The resulting emulsion may be as generally defined herein or as defined by any particular embodiments. For example, in some embodiments the resulting emulsion has a median particle size of from about 100 nm to about 3 μm (including, e.g. about 100 nm to about 1 μm or about 100 nm to about 300 nm). The resulting emulsion may further have an x90 particle size of about 5 μm or less, e.g. about 1.5 μm or less).

Omega-3 Fatty Acid Oil:

The emulsions and emulsion pre-concentrate compositions of the invention comprise an omega-3 fatty acid oil comprising one or more omega-3 fatty acids.

As used herein, "omega-3 fatty acid" includes natural or synthetic, free omega-3 fatty acids and derivatives thereof, unless expressly excluded. Similarly, reference to a particular omega-3 fatty acid includes derivatives thereof, unless expressly excluded.

Suitable omega-3 fatty acid derivatives include pharmaceutically acceptable esters, conjugates (see, e.g., Zaloga et al. US 2004/0254357 and Horrobin et al. U.S. Pat. No. 6,245,811), precursors, salts or other derivatives of omega-3 fatty acids.

Examples of omega-3 fatty acids include:

a) omega-3 polyunsaturated free fatty acids (e.g. having aliphatic tails of 12-22 carbons, especially 18-22 carbons), including omega-3 polyunsaturated, long-chain free fatty acids, e.g. eicosapentaenoic acid C20:5 ("EPA"), docosahexaenoic acid C22:6 ("DHA"), and alpha-linolenic acid;

b) esters of omega-3 fatty acids (e.g. omega-3 polyunsaturated free fatty acids, e.g., long chain) with glycerol such as mono, di and triglycerides; and c) esters of omega-3 fatty acids (e.g. omega-3 polyunsaturated free fatty acids, e.g. long chain) and a primary, secondary or tertiary alcohol such as fatty acid methyl esters and ethyl esters.

The omega-3 fatty acid oil may comprise a mixture any of the foregoing.

Preferred omega-3 fatty acids are polyunsaturated long chain free fatty acids, triglycerides thereof, ethyl esters thereof, and mixtures thereof, including for example EPA, DHA, triglycerides of EPA, triglycerides of DHA, ethyl esters of EPA, ethyl esters of DHA and mixtures thereof.

The omega-3 fatty acid oil may comprise an omega-3 fatty acid in its pure form or e.g., as a component of an oil such as marine or botanical oils (including concentrates thereof), such as fish oil (also known as marine oil), preferably purified fish oil concentrates, perilla oil, marine microalgae oil, or the oil from flax (linseed), chia, kiwifruit, lingonberry, camelina, purslane, or black raspberry seed. Oils containing high concentrations of omega 3 fatty acids such as fish oils or their mixtures, including concentrates thereof, are particularly useful. The term "omega-3 fatty acid oil" encompasses these forms.

Commercial examples of omega-3 fatty acid oils suitable for use in the invention include Incromega F2250, F2628, E2251, F2573, TG2162, TG2779, TG2928, TG3525 and E5015 (Croda International PLC, Yorkshire, England), and EPAX6000FA, EPAX5000TG, EPAX4510TG, EPAX2050TG, K85TG, K85EE, K80EE and EPAX7010EE (Pronova Biocare a.s., 1327 Lysaker, Norway).

In some embodiments, the omega-3 fatty acid oil comprises a mixture of fatty acids. In various embodiments, the fatty acids may be only omega-3 fatty acids or may comprise one or more omega-3 fatty acids in combination with one or more non-omega-3 fatty acids, e.g. omega-6 fatty acids, omega-9 fatty acids, etc. In some embodiments the mixed fatty acid composition comprises fatty acids in a concentration of at least 25% by weight, preferably at least 40% by weight, more preferably at least 50% by weight, still more preferably at least 60% by weight, still more preferably at least 70% by weight, most preferably at least 80% by weight, or even at least 90% by weight, by weight of the composition.

In some embodiments the omega-3 fatty acid oil comprises one or more omega-3 fatty acids in a total concentration of at least 25% by weight, preferably at least 40% by weight, more preferably at least 50% by weight, still more preferably at least 60% by weight, still more preferably at least 70% by weight, most preferably at least 80% by weight, or even at least 90% by weight (e.g. at least 95%, to 100% by weight), by weight of the total fatty acids in the oil. The composition may comprise pure omega-3 fatty acid(s).

Preferably, the omega-3 fatty acid oil comprises at least 50% by weight of EPA and DHA, more preferably at least 60% by weight, still more preferably at least 70% by weight, most preferably at least 80%, such as about 84% by weight, by weight of the total fatty acids in the oil.

The omega-3 fatty acid oil may comprise about 5 to about 100% by weight, more preferably about 25 to about 75% by weight, still more preferably about 40 to about 55% by weight, and most preferably about 46% by weight of EPA by weight of the total fatty acids in the oil.

The omega-3 fatty acid oil may comprise about 5 to about 100% by weight, more preferably about 25 to about 75% by weight, still more preferably about 30 to about 60% by weight, and most preferably about 38% by weight of DHA by weight of the total fatty acids in the oil.

In other embodiments, the percentages above are by weight of the omega-3 fatty acid oil.

The percentages by weight may be based on the free acid or ester forms, although it is preferably based on the ethyl ester form of the omega-3 fatty acids (and other fatty acids, if present) even if other forms are utilized in accordance with the present invention. As used herein, reference to "EPA" and "DHA" include the free acid and ester forms (including specifically, e.g. the ethyl ester forms), unless otherwise stated.

In some embodiments, the EPA and DHA are in a weight ratio of EPA:DHA of from 99:1 to 1:99, e.g., from 1:4 to 4:1, e.g. from 1:3 to 3:1, or e.g. from 1:2 to 2:1. The omega-3 fatty acid oil may also comprise pure EPA or pure DHA.

In some embodiments the omega-3 fatty acid oil is a composition recited in U.S. Pat. Nos. 5,502,077, 5,656,667 or 5,698,594.

The omega-3 fatty acid oil optionally includes one or more components suitable for use in a pharmaceutical, nutritional or dietary supplement composition, including excipients, carriers, diluents, etc. provided that the oil is dispersible and capable of forming an emulsion. For example, in some embodiments the omega-3 fatty acid oil includes a chemical antioxidant, such as alpha tocopherol, an oil, such as soybean oil or partially hydrogenated vegetable oil, a lubricant such as fractionated coconut oil, lecithin, mineral oil or a mixture of the same.

In some embodiments, the omega-3 fatty acid oil is a mixed fatty acid composition comprising LOVAZA® omega-3 fatty acid esters (K85EE, Pronova Biocare A. S., Lysaker, Norway), which preferably comprises the following characteristics (where "EE" refers to ethyl ester):

| Test | Minimum Value | Maximum Value |
| --- | --- | --- |
| Eicosapentaenoic acid C20:5 EE | 430 mg/g composition | 495 mg/g |
| Docosahexaenoic acid C22:6 EE | 347 mg/g composition | 403 mg/g |
| EPA and DHA EE | 800 mg/g composition | 880 mg/g |
| Total omega-3 (n-3) fatty acids EE | 90% (w/w) by wt of the composition | |

In some embodiments, the omega-3 fatty acid oil is a fish oil containing omega-3 acids as described in the US Pharmacopeia ("USP") and National Formulary, Dietary Supplements, e.g. USP32-NF7, released Nov. 1, 2008, official date May 1, 2009, and/or as supplemented in the Second Supplement (released Jun. 1, 2009, official date Dec. 1, 2009); The United States Pharmacopeial Convention; United Book Press Baltimore MD.

In some embodiments, the omega-3 fatty acid oil is obtained from the body oil of fish families such as Engraulidae, Carangidae, Clupeidae, Osmeridae, Salmonidae and Scombridae. In some embodiments the fish oil is purified, e.g., using urea fractionation followed by molecular distillation. In some embodiments, including where obtained from the foregoing fish oils, the omega-3 fatty acid oil comprises ≥90 wt % of the omega-3 fatty acids EPA, DHA, docosapentaenoic acid ("DPA"), stearidonic acid ("SDA"), heneicosapentaenoic acid ("HPA"), eicosatetraenoic acid ("ETA"), and alpha-linolenic acid ("ALA"); and preferably 80 to 88 wt % EPA and DHA, 43 to 49.5% EPA and 34.7 to 40.3 wt % DHA.

In some embodiments, the omega-3 fatty acid oil as described in the USP monograph for omega-3 acid ethyl esters (USP33-NF28 $2^{nd}$ supplement, released Jun. 30, 2009, official date Feb. 1, 2011; The United States Pharmacopeial Convention; Rockville, MD.).

The omega-3 fatty acid oil is present as an active ingredient, and as such it is intended to furnish physiological or pharmacological activity, or other effect, for example in the diagnosis, cure, mitigation, treatment or prevention of a disease or condition or to affect the structure or any function of the body of a subject (e.g. mammalian, especially human). At least one of the omega-3 fatty acids present in the oil contributes to the activity. It will be recognized by those skilled in the art that one or more other constituents in the omega-3 fatty acid oil may be responsible in part for activity. It will also be recognized that different constituents may provide different types and/or levels of activities.

In some embodiments, the omega-3 fatty acid oil is the only active ingredient in the emulsion or emulsion pre-concentrate composition. In some embodiments, one or more of the particular omega-3 fatty acids present, and optionally one or more other fatty acids which may be present, are the only active ingredient(s) in the emulsion or emulsion pre-concentrate composition.

Surfactants:

The emulsion and emulsion pre-concentrate compositions of the invention further comprise one or more surfactants.

Surfactants are well known in the art, see e.g. Handbook of Pharmaceutical Excipients, Edited by Rowe, R. C. et al., 5$^{th}$ Edition. In preferred embodiments, the surfactant (either as a single or combination of surfactants) is characterized by one or more of the following characteristics:

a) it is miscible (i.e., creates a single phase) or partially miscible with the omega-3 fatty acid oil (when used with or without an optional co-solvent);

b) it is safe for use in pharmaceutical, nutritional or dietary supplement formulations (e.g. it has been approved for use in such products, has been safely used in such products, and/or is classified GRAS (Generally Recognized as Safe));

c) it has a peroxide value of <5 and a water content of <2.0; and/or d) it has a high HLB ("hydrophilic-lipophilic balance"), e.g. an HLB value of 10-18.

In some embodiments, the surfactant comprises one or more nonionic, hydrophilic surfactants selected from:

a) Polyoxyethylene castor oil derivatives, including those commercially available under the trade name "CREMOPHOR" (BASF Corp., Mount Olive, N.J.), especially: CREMOPHOR EL or ELP, also referred to as PEG 35 castor oil, polyethoxylated castor oil, macrogoglyceroli ricinoleas, macrogoglyceroli hydroxystearas, POE-35 castor oil, PEG ricinoleate; CREMOPHOR ELP being a purified grade of CREMOPHOR EL having a lower content of water, K and free fatty acids—a polyoxyethylene glycolated castor oil; and CREMOPHOR RH 40, also referred to as polyoxyl 40 hydrogenated castor oil, macrogolglycerol hydroxystearate, polyoxyethylene 40 hydrogenated castor oil, PEG-40 hydrogenated castor oil; and b) Polyoxyethylene Sorbitan Fatty Acid Esters, including those commercially available under the trade name "TWEEN" (ICI Americas), especially:

TWEEN 80, also known as 80[polyoxyetheylene(20)sorbitanmonoleate], polysorbate 80; polyoxyethylene 20 sorbitan monooleate—a partial fatty acid ester of sorbitol and its anhydrides polymerized with ethylene oxide, more specifically a polyoxyethylene-sorbitan-fatty acid mono-oleyl ester, which comprises a mixture of fatty acids including myristic, palmitic, palmitoleic, stearic, oleic and linolenic, predominantly oleic acid;

TWEEN 85, also known as 85[polyoxyetheylene(20)sorbitantrioleate], polysorbate 85; polyoxyethylene 20 sorbitan trioleate—a partial fatty acid ester of sorbitol and its anhydrides polymerized with ethylene oxide, more specifically a polyoxyethylene-sorbitan-fatty acid tri-oleyl esters, which comprises a mixture of fatty acids including myristic, palmitic, palmitoleic, stearic, oleic and linolenic, predominantly oleic acid;

TWEEN 20, also known as polysorbate 20, poly(oxy-1,2-ethanediyl) derivatives; polyoxyethylene 20 laurate; Polyoxyethylene 20 sorbitan monolaurate, sorbitan monodecanoate; p0 TWEEN 60, also known as polysorbate 60, polyoxyethylene 20 stearate, sorbitan monooctadecanoate poly(oxy-1,2-ethanediyl) derivatives; and TWEEN 40, also known as polysorbate 40, Polyoxyethylene 20 sorbitan monopalmitate, sorbitan monohexadecanoate.

In some embodiments, the surfactant is selected from polyoxyethylene castor oil derivatives (especially CREMOPHOR EL, CREMOPHOR ELP), polyoxyethylene sorbitan fatty acid esters (especially TWEEN 80), and mixtures thereof. In some more particular embodiments, the surfactant component comprises about 10-20 (e.g., about 15) wt % CREMOPHOR EL or ELP, and about 80-90 (e.g., about 85) wt % TWEEN 80, based on the total surfactant component.

Optional Components:

The emulsion or emulsion pre-concentrate compositions of the invention may optionally comprise one or more co-solvents. Without intending to be bound by theory, mechanism or the like, the co-solvent may be used, for example, to improve miscibility of the omega-3 fatty acid oil and surfactant. In some embodiments, the co-solvent is pre-mixed with the one or more surfactants.

In some embodiments, the co-solvent is selected from water, $C_{1-4}$ alcohols (straight or branched chain, e.g. ethanol or "EtOH"), $C_{12-22}$ fatty acids (e.g., oleic acid), and mixtures thereof. It has been found that the co-solvent may influence particle size of the resulting emulsion. For example, oleic acid tended to increase particle size and it is hypothesized that other fatty acids may behave similarly. Ethanol and water did not tend to impact particle size, or tended to slightly decrease particle size. It is hypothesized that other alcohols may behave similarly.

It has been surprisingly found that the presence of minor amounts of water in an emulsion pre-concentrate composition of the invention, particularly at equilibrium, tends to improve the clarity of the composition and/or the miscibility of the omega-3 fatty acid oil and surfactant. In some embodiments, water is present in an amount of about 0.1 to about 5 wt %, preferably about 0.7 to about 5 wt %, more preferably about 0.7 to about 1.2 wt %, based on the total weight of the emulsion pre-concentrate composition (determined by Karl Fischer Titration; suitably using a Metrohm 774/756 Oven Sample Processor KF Coulometer or equivalent method, including volumetric methods). The water may be present by direct addition to the pre-concentrate composition, and/or through absorption of moisture during manufacture of the composition, e.g. from the materials used or from the environment. In some embodiments, the water is absorbed during manufacture. For example, the water may be absorbed from the materials used to prepare a capsule during preparation of an encapsulated emulsion pre-concentrate, for example from the materials used to prepare a soft gelatin capsule (e.g. the gelatinous mix comprising gelatin and water). The present invention includes an encapsulated emulsion pre-concentrate composition made by such a process. Preparation of soft gelatin capsules and other capsules is well known in the art. See, e.g. Remington: The Science & Practice of Pharmacy, 20$^{th}$ Ed., Alfonso R. Gennaro, Editor, Lippincott Williams & Watkins, 2000, e.g. 885-891.

The emulsion and emulsion pre-concentrate compositions of the invention may also serve as a carrier or vehicle of other optional ingredients, including one or more pharmaceutical agents, veterinary agents, nutritional or dietary supplements (e.g. herbs, minerals), or excipients such as coloring agents (e.g. dyes, pigments), preservatives, and antioxidants.

In some embodiments, compositions of the invention comprise one or more active ingredients other than the omega-3 fatty acid oil. The other active ingredient(s) may be present in a mixture comprising the omega-3 fatty acid oil, e.g. in the fill component of a capsule wherein the fill comprises an emulsion pre-concentrate composition, in a coating on a capsule comprising an emulsion pre-concentrate composition, incorporated into at least one component of a capsule shell of a capsule comprising an emulsion pre-concentrate composition, or any combination thereof.

For example, the one or more other active ingredients may be substantially dissolved in the composition (e.g. an emulsion pre-concentrate composition, e.g., in the mixture of omega-3 fatty acid oil, surfactant and optional co-solvent), to form a substantially homogeneous solution of the active ingredient(s) in the composition. In some embodiments, an essentially homogeneous solution is formed (i.e., less than 10 wt %, preferably less than 5 wt %, more preferably less than 1 wt % of the other active ingredient(s), based on the weight of the composition, remains undissolved). In some embodiments, the active ingredient(s) are completely dissolved.

In other embodiments, at least a portion of the one or more other active ingredients is present as a suspension in the composition (e.g., an emulsion pre-concentrate composition, e.g., in the mixture of omega-3 fatty acid oil, surfactant, and optional co-solvent). In some embodiments, the suspension comprises solid crystalline particles, solid amorphous particles, or mixtures thereof, of the one or more other active ingredients in the composition. In some embodiments, at least about 80-100% (e.g., at least about 80-99%, including at least about 85, 90, or 95%) of the one or more other active ingredients is present as solid particles in suspension.

In other embodiments, the one or more other active ingredients is present in one or more coatings on a capsule (e.g. a soft gel capsule) containing an emulsion pre-concentrate composition. Examples of coatings containing active ingredients which may be used in the present invention include those disclosed in U.S. Published Patent Application No. US 2007/0212411A1.

An active ingredient, including different other active ingredients, may be present in any combination of the foregoing forms. In preferred embodiments, such compositions of the invention comprise oral dosage forms, particularly capsules and most particularly soft gel capsules.

Examples of other active ingredients include, but are not limited to, the following: analgesics, anti-inflammatory agents, anti-helminthics, anti-arrhythmic agents, anti-asthma agents, anti-bacterial agents, anti-viral agents, anti-coagulants, anti-dementia agents, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, immunosuppressants, anti-protozoal agents, anti-thyroid agents, anti-tussives, anxiolytics, sedatives, hypnotics, neuroleptics, neuroprotective agents, β-blockers, cardic inotropic agents, cell adhesion inhibitors, corticosteroids, cytokine receptor activity modulators, diuretics, anti-Parkinson's agents, gastro-intestinal agents, histamine H-receptor antagonists, keratolytics, lipid regulating agents, muscle relaxants, nitrates and other anti-anginal agents, non-steroid anti-asthma agents, nutritional agents, opioid analgesics, sex hormones, stimulants and anti-erectile dysfunction agents.

In some embodiments, the other active ingredient(s) comprises a lipid regulation agent such as, but not limited to, fatty acids other than the omega-3 fatty acid oil, sterol or stanol fatty acid esters, a statin compound, a squalene synthesis inhibitor, an azetidinone-based cholesterol absorption inhibitor, a LDL (low density lipoprotein) catabolism enhancer, a peroxisome proliferator-activated receptor (PPAR) agonist and/or antagonist, niacin and derivatives such as nicotinamide, a bile acid sequestrant, an MTP inhibitor, an LXR agonist and/or antagonist, and combinations thereof.

Particular examples of other active ingredients include the active pharmaceutical ingredients disclosed in the above-referenced U.S. Published Patent Application No. US 2007/0212411A1.

Emulsion and Emulsion Pre-concentrate Compositions of the Invention:

The relative proportion of ingredients in the compositions of the invention will vary depending on, e.g., the particular type of composition concerned, e.g. whether it is an emulsion pre-concentrate, an emulsion, an oral dosage form formed from the emulsion, etc., and the particular ingredients employed. Determination of workable proportions in any particular instance will generally be within the capability of one skilled in the art in light of this disclosure. All indicated proportions and relative weight ranges described herein are accordingly to be understood as being indicative of preferred or more particular teachings only, and not as limiting the invention in its broadest sense.

Emulsion Pre-concentrate Compositions:

In some embodiments, an emulsion pre-concentrate composition of the invention comprises:

from about 60 to about 85 wt % (e.g. from about 60 to about 80 wt %, e.g. about 70 wt %) of the omega-3 fatty acid oil; and from about 15 to about 40 wt % (e.g., from about 20 to about 40 wt %, e.g. about 30 wt %) of the surfactant; based on the weight of omega-3 fatty acid oil and surfactant in the emulsion pre-concentrate composition; and may optionally further comprise from 0 to about 5 wt % (e.g. about 0.1 to about 5 wt %, or about 0.7 to about 5 wt %, or about 0.7 to about 1.2 wt %) co-solvent, based on the total weight of the emulsion pre-concentrate composition.

For example, an emulsion pre-concentrate composition of the invention may comprise:

from about 60 to about 80 wt % of the omega-3 fatty acid oil;

from about 20 to about 40 wt % of the surfactant;

based on the weight of the omega-3 fatty acid oil and surfactant in the emulsion pre-concentrate composition; and optionally from about 0.7 to about 5 wt % (e.g. about 0.7 to about 1.2 wt %) co-solvent, based on the total weight of the emulsion pre-concentrate composition;

or in some embodiments:

about 70 wt % of the omega-3 fatty acid oil;

about 30 wt % of the surfactant;

based on the weight of the omega-3 fatty acid oil and surfactant in the emulsion pre-concentrate composition; and optionally about 0.7 to about 5 wt % (e.g. about 0.7 to about 1.2 wt %) co-solvent; based on the total weight of the emulsion pre-concentrate composition.

In some embodiments, the weight ratio of omega-3 fatty acid oil and surfactant in the composition is greater than 2:1, e.g. in the range of from more than 2:1 to about 6:1 or to about 4:1.

As noted above, the emulsion pre-concentrate or emulsion may comprise one or more omega-3 fatty acid oils, surfactants or and/co-solvents. In some of the above emulsion pre-concentrate composition embodiments, the omega-3 fatty acid oil is K85EE, the surfactant is selected from polyoxyethylene castor oil derivatives (especially CREMO- PHOR EL, CREMOPHOR ELP), polyoxyethylene sorbitan fatty acid esters (especially TWEEN 80), and mixtures thereof, and the optional co-solvent is water. In one embodiment of such compositions, the surfactant component comprises about 10-20 (e.g., about 15) wt % CREMOPHOR EL or ELP, and about 80-90 (e.g., about 85) wt % TWEEN 80, based on the total surfactant component.

A pre-concentrate of the invention may be formed by combining the omega-3 fatty acid oil and the surfactant components and mixing until the combination is uniform. In general, a surfactant in solid or semi-solid form is warmed to liquefy (e.g., to about 30° C.), and then mixed with the omega-3 fatty acid oil. Optional ingredients may be combined and mixed with individual or a mixture of components.

In some embodiments, an emulsion pre-concentrate of the invention is formed by a process comprising the steps of combining the surfactant(s) with a co-solvent (e.g. water), mixing until the combination is uniform, then combining the mixture with the omega-3 fatty acid oil (e.g., adding the mixture to the oil), and then mixing the combination until uniform. In such embodiments, where the surfactant(s) is in solid or semi-solid form, the surfactant is first heated (e.g. to about 30° C.) to liquefy the surfactant(s), and then combined and mixed with the co-solvent.

In some embodiments, the invention comprises a hard or soft capsule, wherein the fill comprises an emulsion pre-concentrate of the invention. The manufacture of hard or soft capsules is generally known by those of ordinary skill in the art. For example, soft capsules may be made by various processes including the plate process, the rotary die process, the reciprocating die process, and the continuous process. See, for example, Remington: The Science & Practice of Pharmacy, $20^{th}$ Ed., Alfonso R. Gennaro, Editor, Lippincott Williams & Watkins, 2000, e.g. 885-891; Ebert (1978), "Soft Elastic Gelatin Capsules: A Unique Dosage Form," Pharmaceutical Technology 1(5); Reich (2004), "Chapter 11: formulation and physical properties of soft capsules," Pharmaceutical Capsules, 2d Ed., Pharmaceutical Press, 201-212. See also U.S. Pat. Nos. 5,478,508 and 5,882,680, and U.S. Patent Application Publication Nos. US 2005/0106233A1 and US 2007/0259097A1. disclosing methods of manufacturing seamless capsules. Capsular materials such as are known in the art may be utilized; examples of capsular materials include natural or synthetic gelatin, pectin, casein, collagen, protein, modified starch, polyvinyl pyrrolidone, acrylic polymers, cellulose derivatives (e.g. hydroxypropyl methyl cellulose (HPMC), methyl cellulose (MC)), alginates and other polysaccharides, and combinations thereof, optionally with one or more plasticizers and/or water. Capsular materials may also include one or more preservatives, colorants, opacifying agents, flavorings, sweeteners, sugars, gastroresistant substances or combinations thereof. In presently preferred embodiments, the capsule is a soft gelatin capsule ("soft gelcap" or "soft gel capsule").

The shape and size of the capsules can vary in accordance with the invention. The shape of the capsule may be, but is not limited to, spherical or round, oval, tubular, oblong, twist off, or a non-standard shape (e.g., a fish, tree, star, heart, or bear), preferably oblong. The size of the capsule used will vary in accordance to the volume of the fill composition intended to be contained therein.

For example, in some embodiments of the present invention, hard or soft gelatin capsules may be manufactured in accordance with conventional methods as a single body unit comprising the standard capsule shape. A single-body soft gelatin capsule typically may be provided, for example, in sizes from 3 to 22 minims (1 minimim being equal to 0.0616 ml) and in shapes of oval, oblong or others. The gelatin capsule may also be manufactured in accordance with conventional methods, for example, as a two-piece hard gelatin capsule, sealed or unsealed, typically in standard shape and various standard sizes, conventionally designated as (000), (00), (0), (1), (2), (3), (4), and (5). The largest number corresponds to the smallest size. Non-standard shapes may be used as well.

For example, the emulsion pre-concentrate capsules are suitably formed by direct encapsulation of a mixture comprising the omega-3 fatty acid oil and surfactant into soft gelatin capsules. In a compounding step, the oil and surfactant was blended. Continuous mixing is applied; or alternatively or additionally about 1 wt % water is added to the mixture, e.g., to assist in formation of a homogeneous solution. Equipment and conditions are suitably selected to minimize risk of oxidation and to eliminate foaming or bubbling, for example sealed mixing tanks with nitrogen blanket, recirculation and vacuum capabilities are suitable. The mixture is then encapsulated, suitably using rotary encapsulation. For formation of a capsule, molten gel mass (e.g., comprising gelatin, glycerol and water) is machine-cast into two continuous ribbons, which are brought into convergence between a pair of dies and an injection wedge through which the fill mixture is pumped in the determined amounts. Filling and sealing of the capsule is essentially coincident, to form capsules of the desired size, shell weight, fill weight and seal thickness. The capsules are dried to a suitable hardness (e.g. not less than 8.5 newtons), for example by first tumble drying in a rotary dryer (e.g. 15 min/segment for a total of about 60-75 minutes) followed by tunnel drying in shallow trays. The capsules are suitably polished or spray washed to remove lubricant oil used during the process, using e.g. isopropyl alcohol.

In some embodiments, capsules of the invention may be coated with one or more coatings comprising a coating material, such as a film forming material and/or binder, and optionally other conventional additives such as are known in the art. The coating(s) may be applied by any conventional technique such as pan, fluid bed, or spray coating, e.g. as a solution, suspension, spray, dust or powder. The coating(s) may be formulated for immediate release, delayed release, enteric release, sustained release, protective coating, seal coating, and/or barrier coating in accordance with methods well known in the art. Conventional coating techniques are described, e.g., in Remington: The Science & Practice of Pharmacy, $20^{th}$ Ed., Alfonso R. Gennaro, Editor, Lippincott Williams & Watkins, 2000, e.g. 894-902. Examples of film-forming materials and conventional additives include those disclosed in U.S. Published Patent Application Nos. US 2007/0212411A1, US 2005/0106233A1 and US 2007/0259097A1. As discussed above, one or more coatings may comprise one or more other active ingredients.

When an emulsion pre-concentrate of the invention is orally administered, an emulsion may be formed upon contact with the aqueous gastric fluids with or without co-administration with a suitable aqueous liquid. An emulsion pre-concentrate of the invention may also be diluted with a suitable aqueous liquid before administration (in some embodiments forming an emulsion), which is then administered. Suitable aqueous liquids are edible, and include water itself, juices or other beverages or drinkable liquids containing water. The emulsion formed may have any of the characteristics of emulsions described herein, e.g. a median particle size of from about 100 nm to about 3 μm.

Emulsion Compositions:

In some embodiments, an emulsion composition of the invention comprises:

from about 15 to about 30 wt % of the omega-3 fatty acid oil;

from about 5 to about 10 wt % of the surfactant;

an aqueous liquid providing from about 65 to about 80 wt % water;

and optionally from about 0 to about 5 wt % co-solvent (other than water);

wherein the weight percentages are based on the total weight of the emulsion composition.

In some of these embodiments, the omega-3 fatty acid oil is K85EE, the surfactant is selected from polyoxyethylene castor oil derivatives (especially CREMOPHOR EL, CREMOPHOR ELP), polyoxyethylene sorbitan fatty acid esters (especially TWEEN 80), and mixtures thereof, and the optional co-solvent is selected from $C_{12-22}$ fatty acids (especially oleic acid), $C_{1-4}$ alcohols (especially ethanol), and mixtures thereof.

Suitable aqueous liquids are edible, and include water itself, juices or other beverages or drinkable liquids containing water. It will be understood that, to obtain an emulsion, adequate water is required. Generally, an emulsion composition will comprise at least about 70 wt % water, based on the weight of the composition.

An emulsion composition of the invention may be formed by combining and mixing until uniform the omega-3 fatty acid oil, surfactant and aqueous liquid components, and any optional components, in any order. In other embodiments, the emulsion composition may be formed by mixing an emulsion pre-concentrate of the invention with an aqueous liquid (comprising, for example, at least about 1 wt % pre-concentrate).

Uses

Other embodiments of the present invention provide for the use of an emulsion or emulsion pre-concentrate composition of the invention for the manufacture of a pharmaceutical (or medicament), nutritional or dietary supplement product suitable for treatment of any of the diseases, conditions or the like for which the omega 3 fatty acid oil may be used.

Other embodiments of the present invention provide for a method of treatment comprising administering an emulsion or an emulsion pre-concentrate composition of the invention (including diluted versions thereof), to a subject in need thereof, for treatment of any of the diseases, conditions, or the like for which the omega 3 fatty acid oil may be used.

As used herein, to "treat" in reference to a disease or condition includes: (1) to ameliorate or prevent the disease or condition or one or more of the biological manifestations of the disease or condition, (2) to interfere with (a) one or more points in the biological cascade that leads to or is responsible for the disease or condition or (b) one or more of the biological manifestations of the disease or condition, (3) to alleviate one or more of the symptoms or effects associated with the disease or condition, or (4) to slow the progression of the disease or condition or one or more of the biological manifestations of the disease or condition.

As noted above, "treatment" of a disease or condition includes prevention of the disease or condition. The skilled artisan will appreciate that "prevention" is not an absolute term. In medicine, "prevention" is understood to refer to the prophylactic administration of a drug or active ingredient to substantially diminish the likelihood or severity of a disease or condition or biological manifestation thereof, or to delay the onset of such disease or condition or biological manifestation thereof. Accordingly, prevention includes reducing the risk of occurrence of a disease or condition.

As used herein, "subject" refers to a human or other animal (e.g. mammals).

The emulsion or emulsion pre-concentrate composition is generally administered in a safe and effective amount. i.e., an amount sufficient to treat the subject's disease or condition but low enough to avoid serious side effects (at a reasonable benefit/risk ratio) within the scope of sound medical judgment. A safe and effective amount will vary with the particular composition chosen (e.g. consider the potency, efficacy, and half-life of the active ingredients); the route of administration chosen; the disease or condition being treated; the severity of the disease or condition being treated; the age, size, weight, and physical condition of the subject being treated; the medical history of the subject to be treated; the duration of the treatment; the nature of concurrent therapy; the desired therapeutic effect; and like factors, but can nevertheless be routinely determined by the skilled artisan.

Diseases or conditions for which the omega-3 fatty acid oil may be used include diseases or conditions for which one or more of the constituent omega-3 fatty acids may be used. Examples of diseases or conditions for which the omega-3 fatty acid(s) and the omega-3 fatty acid oil may be used include those now known as well as new uses which may be identified, including treatment of one or more abnormal plasma lipid levels or abnormal cardiovascular function. For example, the omega-3 fatty acid oil may be used for treatment of at least one condition or disease independently selected from the group consisting of hypertriglyceridemia, hypercholesterolemia, mixed dyslipidemia, cardiovascular disease, coronary heart disease (CHD), vascular disease, atherosclerotic disease and related conditions, and/or for the prevention or reduction of cardiovascular and/or vascular events (including MACEs, MCEs). Diseases or conditions may be any of those disclosed in U.S. Pat. Nos. 5,502,077, 5,656,667 or 5,698,594.

Cardiovascular disease (CVD) is a broad term that encompasses a variety of diseases and conditions. It refers to any disorder in any of the various parts of the cardiovascular system, which consists of the heart and all of the blood vessels found throughout the body. Diseases of the heart may include coronary artery disease, CHD, cardiomyopathy, valvular heart disease, pericardial disease, congenital heart disease (e.g., coarctation, atrial or ventricular septal defects), and heart failure. Diseases of the blood vessels may include arteriosclerosis, atherosclerosis, hypertension, stroke, vascular dementia, aneurysm, peripheral arterial disease, intermittent claudication, vasculitis, venous incompetence, venous thrombosis, varicose veins, and lymphedema. Some patients may have received treatment for their CVD, such as vascular or coronary revascularizations (angioplasty with or without stent placement, or vascular grafting). Some types of cardiovascular disease are congenital, but many are acquired later in life and are attributable to unhealthy habits, such as a sedentary lifestyle and smoking. Some types of CVD can also lead to further heart problems, such as angina, major adverse cardiovascular events (MACEs) and/or major coronary events (MCEs) such as myocardial infarction (MI) or coronary intervention, or even death (cardiac or cardiovascular), which underscores the importance of efforts to treat and prevent CVD.

Omega-3-fatty acid oil may be used for primary or secondary prevention. Primary prevention efforts are focused on reducing known risk factors for CVD, or preventing their development, with the aim of delaying or preventing the onset of CVD, MACEs or MCEs. Secondary prevention efforts are focused on reducing recurrent CVD and decreasing the risk of mortality, MACEs or MCEs in patients with established CVD.

MACEs include cardiac death, other cardiovascular death, MCEs (which include myocardial infarction (MI) and coronary intervention such as coronary revascularization, angioplasty, percutaneous transluminal coronary angioplasty (PTCA), percutaneous coronary intervention (PCI) and coronary artery bypass graft (CABG)), hospitalization for unstable angina, stroke, transient ischemic attack (TIA) and hospitalization for peripheral artery disease (PAD).

CHD includes symptomatic ischemic heart disease, including MI, stable or unstable angina, demonstrated myocardial ischemia by noninvasive testing, and history of coronary artery procedures (see, e.g., NCEP ATP III).

The present invention includes use of the compositions of the invention for treating any of the aforementioned diseases or conditions.

In some embodiments, the emulsion or emulsion pre-concentrate composition is used to reduce triglycerides (TG). Accordingly, in some embodiments treatment comprises administering a composition of the invention to reduce TG, for example to reduce triglycerides in patients having very high triglycerides (>500 mg/dL), high triglycerides (≥200 mg/dL) or borderline high triglycerides (150-199 mg/dL). For example, the triglyceride levels in patients having very high triglycerides may be reduced to high, borderline-high, or normal levels; or triglyceride levels in patients having high triglycerides may be reduced to borderline-high or normal levels; or triglyceride levels in patients having borderline high triglycerides may be reduced to normal levels (<150 mg/dL).

In some embodiments, treatment comprises administering an emulsion pre-concentrate or emulsion composition of the invention to improve one or more other lipid parameters. In some embodiments, HDL-C (high density lipoprotein cholesterol) is increased and/or one or more of the following lipid parameters are reduced: non-HDL-C (non-high density lipoprotein cholesterol), LDL-C (low density lipoprotein cholesterol), TC (total cholesterol), VLDL-C (very low density lipoprotein cholesterol), TC:HDL-C ratio, and ApoB (Apolipoprotein B). In some embodiments, treatment comprises administering a composition of the invention to reduce TG, and further to improve one or more of the aforementioned other lipid parameters as described.

For example, in some embodiments, non-HDL-C is reduced, or both non-HDL-C and TG are reduced. In some embodiments, non-HDL-C and TG are reduced in in patients having mixed dyslipidemia with high TG. Such patients may be receiving concomitant therapy, e.g., statin therapy.

In some embodiments, treatment comprises administering a composition of the invention to improve post-prandial lipid parameters, e.g. to increase post-prandial HDL and/or reduce one or more of post-prandial TG, non-HDL-C, LDL-C, TC, VLDL-C, TC:HDL ratio, and ApoB level.

In some embodiments, TG is reduced by at least about 5% (e.g. at least about 10, 15, 20, 25, 30, 40, 50 or 60%) following treatment (compared to baseline TG value before treatment). In some embodiments, TG reduction following treatment with a composition of the invention is more than any TG reduction following treatment with the non-emulsified omega-3 fatty acid oil administered at an equivalent or higher actual dose, for example at least about 5%, 10% or 15% more TG reduction (compared to baseline TG values before treatments, respectively).

In some embodiments, improvement in one or more other lipid parameters following treatment with a composition of the invention is more than any improvement following treatment with the non-emulsified omega-3 fatty acid oil administered at an equivalent or higher actual dose (increase or reduction as applicable; compared to baseline lipid value(s) before treatments, respectively).

In some embodiments, the improvements in TG or other lipid parameter(s) are achieved using an equivalent dose, or a lower dose of omega-3-fatty acid oil, relative to the dose of non-emulsified omega-3 fatty acid oil.

In some embodiments, the improvements in TG or other lipid parameter(s) are achieved by 4 weeks, 8 weeks, 12 weeks, 24 weeks, or 1 year on-treatment.

Other embodiments of the invention provide for a method of increasing the oral absorption (exposure) and/or oral bioavailability of an omega-3 fatty acid in a subject in need of treatment with an omega-3 fatty acid, comprising orally administering an emulsion or emulsion pre-concentrate composition of the invention to the subject, wherein the oral absorption and/or oral bioavailability is increased compared to the oral absorption and/or oral bioavailability after administering the omega-3 fatty acid oil used in the composition.

In some embodiments, an increase in absorption is exhibited by an increase in AUC of the total omega-3 fatty acids measured. In some embodiments, the omega-3 fatty acids which are measured are EPA and/or DHA. In some embodiments, the blood serum level of total EPA and/or DHA is increased, preferably the blood serum level of total EPA and/or DHA is increased by at least about 2, 3 or 4- fold (e.g., from at least about 2 fold, to about 5-15 fold) compared to the blood serum level of total EPA and/or DHA after administering the omega-3 fatty acid oil used in the composition. In some embodiments, the blood serum level of free EPA and/or DHA is also increased, compared to the blood serum level of free EPA and/or DHA after administering the omega-3 fatty acid oil used in the composition.

The emulsion and emulsion pre-concentrate compositions of the invention may be employed for administration in any appropriate manner. In preferred embodiments, the composition is administered orally, e.g. in unit dosage form such as hard or soft capsule form (including gelatin capsules); or a drinkable form such as an edible liquid formed by mixing an emulsion or emulsion pre-concentrate composition of the invention with other ingredients (such as aqueous liquids described herein) to form a drinkable mixture, including beverages. In preferred embodiments, the emulsion pre-concentrate composition is administered in encapsulated form, especially as a soft gelatin capsule.

The emulsion pre-concentrate or emulsion composition is administered in an amount and frequency to provide the desired treatment. In general, the pre-concentrate or emulsion composition is administered to provide a daily amount of omega-3 fatty acid oil, preferably a daily amount of omega-3 fatty acids, of from about 0.1 g, 0.5 g, 0.75 g, or about 1 g, to about 1 g, 1.5 g, 2 g, 3 g, 4 g, 8 g, or 10 g per day, including for example, about 0.1 g to about 10 g, about 0.5 g to about 8 g, about 0.75 g to about 4 g, about 0.1 g to about 2 g, about 0.5 g to about 1.5 g, or about 1 g per day. In some embodiments, administration is to provide about 1-4 g (including particularly, about 1, 2, 3, or 4g) of omega-3 fatty acid oil (preferably omega-3 fatty acids) per day.

The daily dosage of omega-3 fatty acid oil will generally be administered in from 1-10 dosages, e.g. 1-4 or 1-2 dosages per day. For example, 1 or 2 capsules may be administered twice per day (i.e. 2 or 4 capsules per day) to provide the desired total daily dosage.

The emulsion preconcentrate or composition may be administered for a period sufficient to provide and maintain the desired treatment. In general, the compositions of the invention will be administered for at least 4 weeks, including at least 8 weeks, 12 weeks, or 24 weeks or at least one year.

In some embodiments, an emulsion pre-concentrate composition of the invention is orally administered with a suitable aqueous liquid (an edible liquid, including water itself, juices or other beverages or drinkable liquids containing water). For example, an emulsion pre-concentrate composition may be administered with up to about 500 ml of a suitable aqueous liquid.

Methods of treatment of the invention may be achieved using the emulsion preconcentrate or emulsion compositions of the invention as a monotherapy, or in dual or multiple combination therapy with one or more therapeutic agents or therapies, for example with one or more active ingredients disclosed herein above, which may be administered in effective amounts. One or more compounds from a given class, or from different classes may be used in combination with an emulsion pre-concentrate or emulsion composition of the invention. Use in combination includes combination products (e.g. dosage forms, including those described herein above) as well as regimens. Accordingly, the active ingredient(s) may be combined in a single emulsion pre-concentrate or emulsion composition, or may be in different compositions which are administered to a patient concurrently or at different times.

In some embodiments, a method of treatment of the invention is achieved using the emulsion pre-concentrate or emulsion composition as monotherapy, wherein the omega-3 fatty acid oil is the only active ingredient (as described above).

In other embodiments, a method of treatment of the invention is achieved with combination therapy with at least one other active ingredient, such as described herein, e.g. a lipid regulation agent, which may be used in effective amounts including those known in the art (e.g. in prescribing information). In particular embodiments, at least one other lipid active ingredient comprises a statin.

EXAMPLES

Example 1

Method for Determining Particle Size (Including Median and x90

A Malvern particle size analysis instrument (Mastersizer 2000 Ver. 5.40; Malvern Instruments Inc., Westborough, Mass., USA), which uses a static laser light scattering technique to measure particle size, or an equivalent, is employed to determine the particle size of an emulsion, including an emulsion formed from a pre-concentrate.

For example, an emulsion pre-concentrate of the invention is combined with de-ionized water, in a ratio of 1 g pre-concentrate to 20 ml water at room temperature (approximately 25° C.). This mixture is inverted 20 times (e.g. in a test tube, by hand, taking care not to shake, causing foaming or bubbles) to disperse the components and form an emulsion. The particle size distribution (frequency versus particle diameter, based on normalized volume distribution) is determined by the Mastersizer 2000, and is reported as particle size statistics such as the median ($50^{th}$ percentile of the cumulative size distribution, sometimes referred to as D50) and the x90 ($90^{th}$ percentile of the cumulative size distribution, sometimes referred to as the D90). Water was used as the media in the Mastersizer. The median and x90 particle size of other emulsion compositions of the invention (e.g. test liquid emulsions) are also determined using the Mastersizer 2000, using the test composition directly.

Example 2

Method for Determining Relative Bioavailability

Following ingestion, the digestion and absorption of omega-3 fatty acids from omega-3 fatty acid esters involve 3 different steps: hydrolysis from the alcohol to which they are bound, absorption/transport into the enterocytes of the intestine, and subsequent intestinal use or packaging for transport to the body (as will be understood by those skilled in the art, digestion and absorption following ingestion of the corresponding free fatty acids would involve the last two steps).

After rapid and complete hydrolysis of omega-3 ethyl esters by esterases in the intestine, the free fatty acids are absorbed/transported into the intestinal enterocytes, rapidly reesterified, and enter the systemic circulation via the thoracic duct as chylomicrons. Following transit through the thoracic duct, the chylomicrons enter the plasma. The normal half-life of a chylomicron in the circulation is approximately 10 minutes. Lipoprotein lipase, present on the endothelial surfaces of capillary beds, hydrolyzes the triglyceride core of the chylomicron, liberating the fatty acids for tissue uptake.

The absorption of omega-3 fatty acids into the systemic circulation can be directly measured by determining the plasma levels of their free form and the total levels after liberating the free fatty acid form from its esterified form (chylomicrons).

In addition, the fatty acid composition of the serum phospholipids correlates with levels incorporated in membranes (e.g., erythrocyte, monocyte, and thrombocyte membranes) (See, e.g. Katan, M B, et al., J Lipid Res. 1997; 38:2012-22 and Tremoli, E et al., Am J Clin Nutr. 1995; 67:607-13). The omega-3 fatty acid composition of erythrocyte and thrombocyte membranes, in turn, correlates with whole body content of these compounds. Analysis of blood phospholipids is, therefore, an appropriate way to assess the performance of products intended to increase total body stores of omega-3 fatty acids. Analysis of plasma phospholipids has been described, e.g. by Harris, W. et al. Clinical Biochemistry 43 (2010) 338-340; Harris, W. et al., American Journal of Clinical Nutrition 2007; 86: 1621-5; Cao, J. et al., Clinical Chemistry 52:12 2265-2271 (2006); Harris, W. et al., Preventive Medicine 39 (2004) 212-220; and Park, Y. et al., Journal of Lipid Research 44, 2003 455-463.

Thus, when investigating the absorption of omega-3 fatty acids comprising EPA and DHA (e.g., from omega-3-acid ethyl esters comprising EPA and DHA ethyl esters), the increase of EPA and DHA in plasma or in serum phospholipids may be used as a measure of absorption. These measures of absorption may be used as a measure of oral bioavailability.

Methodology for measuring the absorption of omega-3 fatty acids is described in more detail in the following experimental(s).

The following definitions may be used herein:
Cmax—maximum observed concentration
AUC—area under the concentration-time curve
$AUC_{(0-x)}$—AUC from zero (pre-dose) to some fixed nominal time AUC$_{(0-t)}$—AUC from zero (pre-dose) to last time of quantifiable concentration within a subject across all treatments AUC$_{0-\infty}$—AUC from zero (pre-dose) extrapolated to infinite time Tmax—time of occurrence of Cmax t½—terminal phase half-life CV—coefficient of variance (CVb=between subject; CVw=within subject)

CI—confidence interval

LS—least square

Other statistical terms are used in accord with their commonly used meaning, unless otherwise indicated expressly or by context.

Example 3

Relative Bioavailability Studies

In two separate studies in dogs, the relative bioavailability of 100% K85EE oil was compared to 7 emulsion formulations of K85EE oil (5 pre-concentrate capsules and 2 liquid formulations. Each formulation was given as a single oral administration (where liquid formulations, by gavage) to fasted male beagle dogs at target doses of 26.8 and 20.5 mg/kg of EPA and DHA ethyl esters (EE), respectively.

Non-naïve male beagle dogs (body weight approximately 9-13 kg) were used in the studies. Sampling was conducted under fasted conditions for an 8 hour sampling period. I.e., the dogs were fasted overnight prior to each study day and food (a standard canine diet) was returned to them after an 8-hour blood collection period. Filtered tap water was available ad libitum.

For pharmacokinetic analysis, blood samples were nominally collected at 0, 0.5, 1, 2, 4, 6 and 8 hours post dose (or if no dosing, at an arbitrary time that would ordinarily be at the time of dosing). The collection tubes are gently mixed and placed on wet-ice immediately after collection. Plasma samples are prepared within one hour of collection by centrifugation, dispensed into polypropylene tubes and frozen immediately until analysis of free and total EPA (Eicosapentaenoic acid) and DHA (Docosahexaenoic acid).

Plasma was assayed for total EPA and DHA using a triglyceride digestion based method which included acidic and basic digestion, followed by liquid-liquid extraction with hexane. Chromatographic separation and detection was achieved with an ultra high performance liquid chromatography-tandem mass spectrometry (UHPLC/MS/MS) system with a lower limit of quantification (LLQ) of 0.5 μg/m L. Plasma samples were also assayed for free EPA and DHA (without triglyceride digestion) using a liquid-liquid extraction followed by UHPLC/MS/MS with a LLQ of 0.05 μg/mL. To account for endogenous levels of EPA and DHA, plasma concentration data were corrected by subtraction of the EPA and DHA pre-dose values to yield corrected C$_{max}$ (C$_{max\ corr}$) and the pre-dose plasma concentration was multiplied by 8 hours and then was subtracted from AUC$_{0-8}$ to yield corrected AUC$_{0-8}$ (AUC$_{0-8\ corr}$) values. The total minus free concentration is assumed to be a function of the EPA or DHA concentration incorporated into ("bound") and circulating within chylomicrons in the systemic circulation.

Study A:
Test Formulas:

| Formulation | Wt. % of Total | | |
|---|---|---|---|
| | K85EE Oil | Cremophor ELP | Water |
| 1 - 100% K85EE | 100 | 0 | 0 |
| 2 - 25% K85EE liquid emulsion | 25 | 6 | 69 |

Formula 2 was prepared by mixing Cremophor ELP with K85EE oil until uniform, then adding the mixture to water under mixing.

Either K85EE oil or the liquid emulsion formula 2 were administered to dogs (n=8/group, crossover design with a 2 week washout period between dosings; n=4/group on each treatment day).

On study day 1, blood samples are collected in the fasted dogs over the course of 8 hours, with no formulation being dosed. On study day 2, the reference and emulsion formulation are administered to 4 dogs each via oral gavage, rinsing the dosing tube with about 10 ml water. On study day 3 another blank profile is collected as was done on day 1. Following an additional week (washout), crossover takes place on study day 4.

The mean doses of EPA and DHA initially administered were 29.6 and 22.7 mg/kg for K85EE and 30.2 and 23.0 mg/kg for formulation 2; the mean crossover doses subsequently administered were 29.4 and 22.5 mg/kg for K85EE and 30.0 and 22.8 mg/kg for formulation 2.

Both free and bound EPA and DHA are determined for each sample. Plasma is generated from each sample by centrifugation and frozen until the time of analysis. Two aliquots are taken for analysis: Aliquot A is assayed for free EPA and DHA. Aliquot B undergoes a digestion procedure using alkaline hydrolysis in which any present TAG circulating in the blood within chylomicrons is digested followed by analysis of liberated EPA and DHA.

For the total and free EPA/DHA analyses, essentially fatty acid free, ~99% (by agarose gel electrophoresis), lypophilized powder human serum albumin (Sigma) was used as a substitute matrix for the assay. Due to the endogenous fatty acid levels in dog plasma, this matrix was validated as an appropriate substitute for preparation of standards and quality control (QC) samples. QC samples, prepared at 3 different analyte concentrations and stored with study samples, were analysed with each batch of samples against separately prepared calibration standards. For an acceptable analysis, no more than ⅓ of the QC results were to deviate from the nominal concentration by more than 15%, and at least 50% of the results from each QC concentration should be within 15% of nominal.

The extraction method is based on S. A. Lagerstedt et al., Molecular Genetics and Metabolism 73, 38-45 (2001), modified for compatibility with UHPLC-MS/MS systems.

For extraction of free DHA and EPA, 50 μL of test sample (human plasma, 25 μL), standard or QC sample is aliquoted into vials/tubes. 50 μL acetonitrile is added to double blank, and 50 μL internal standard working solution (500 ng/mL of deuterated EPA and DHA) is added to all other vials/tubes. Samples are acidified and then extracted with hexane. After mixing, the supernatant is transferred to a plate containing silanized glass inserts, evaporated at 40° C. under N2, and reconstituted with 50/50 acetonitrile/water. Analysis for free EPA and DHA can then be performed using the UHPLC-MS/MS.

For extraction of total DHA and EPA, 50 μL of test sample (human plasma, 25 μL), standard or QC sample is aliquoted into micronic vials/tubes. 100 μL acetonitrile is added to double blank, and 100 μL internal standard working solution (500 ng/mL of deuterated EPA and DHA) is added to all other vials/tubes. The initial digestion involves addition of 90/10 acetonitrile/6N HCl to all samples. The plate is sealed and mixed, followed by incubation for approximately 45 min at about 104° C. After cooling to room temperature, 90/10 methanol/10N NaOH is added to all wells, the plate is capped, mixed and then incubated as above. After cooling to room temperature the plate is mixed and centrifuged, and 200 μL of the supernatant is transferred to a clean plate. 6N HCl followed by hexane is added to all wells. The plate is capped, mixed for about 5 min, then centrifuged. The supernatant is transferred to a plate containing silanized glass inserts, and evaporated at 40° C. under $N_2$. Samples are reconstituted with 50/50 acetonitrile/water, mixed, centrifuged and then analyzed for total EPA and DHA.

LC separation can be achieved in under 1.5 minutes using an Acquity UPLC BEH C18, 50×2.1 mm, 1.7 μm column with gradient conditions. Alternative, equivalent UHPLC equipment may be used, and minor changes to chromatographic conditions may be made.

Plasma concentration vs time profiles are generated for 1) free EPA and DHA from aliquot A; 2) bound EPA and DHA from aliquot B; 3) subtotal of EPA plus DHA in TAG from aliquot B and 4) overall total of free EPA and DHA plus bound EPA and DHA. AUC (0-t), Cmax and Tmax are calculated for each of the four conditions per animal per formulation. Relative bioavailability ("F") may be calculated for each test formulation as:

F=AUC(0-t) test formulation/AUC(0-t) reference formulation

Results are shown in Table 1:

systemic absorption and bioavailability of the emulsion formulation 2 for EPA and DHA compared to K85EE.

Study B:

In the second study, six formulations of K85EE (five pre-concentrate capsules and one liquid (by gavage), were administered to dogs (n=4/group). The study was conducted on six separate study days.

Test Formulas:

| | Wt % of Total | | | |
| --- | --- | --- | --- | --- |
| Formulation | K85EE Oil | Cremophor ELP | Polysorbate 80 | Ethanol |
| 3 - capsule | 66 | 15 | 15 | 4 |
| 4 - capsule | 70 | 0 | 30 | 0 |
| 5 - capsule | 77 | 20 | 0 | 3 |
| 6 - capsule | 88 | 5 | 5 | 2 |
| 7 - as liquid emulsion [a] | 66 | 15 | 15 | 4 |
| 8 - capsule | 90 | 0 | 7 | 3 |

[a] Dispersed in water at a final concentration of 25% emulsion pre-concentrate formulation and 75% water.

Formulations 3-6 and 8 were prepared by adding the surfactant(s) to the K85EE oil under mixing (magnetic stirrer). When Cremophor ELP was used it was heated to 30° C. before addition to the oil. The mixture was filled into hard gelatine capsules using a pipette.

Formulation 7 was prepared by mixing the surfactants with K85EE oil until uniform, then adding the mixture to water under mixing. When Cremophor ELP was used it was heated to 30° C. as needed to melt and mix with the other components.

Free and total EPA and DHA were assayed in the manner described above. Pharmacokinetic (PK) analysis of free and total EPA and DHA plasma concentration-time data was performed, following appropriate baseline corrections of endogenous EPA and DHA, using non-compartmental methods to obtain estimates of PK parameters where possible. Relative bioavailability ("F") is calculated as:

TABLE 1

| | Relative Exposure Ratios[a] | | | | | | | |
| --- | --- | --- | --- | --- | --- | --- | --- | --- |
| | Total EPA | | Total DHA[b] | | Free EPA | | Free DHA | |
| Formulation | $C_{max}$ | $AUC_{0-8}$ | $C_{max}$ | $AUC_{0-8}$ | $C_{max}$ | $AUC_{0-8}$ | $C_{max}$ | $AUC_{0-8}$ |
| 1—100% K85EE | 1.00 | 1.00 | 1.00 | 1.00 | 1.00 | 1.00 | 1.00 | 1.00 |
| 2—25% K85EE liquid emulsion[c] | 3.38 | 3.65 | 4.82 | 4.61 | 1.80 | 1.94 | 2.82 | 2.69 |

The data values represent the mean for each exposure ratio, with a n = 8 dogs/group (crossover design with a 2 week washout period), unless otherwise stated.
[a] = Ratios of exposure (25% K85EE/100% K85EE) for EPA (total and free) and DHA (total and free) were calculated from corrected $C_{max}$ and $AUC_{0-8}$ values ($C_{max\ corr}$ and $AUC_{0-8\ corr}$).
[b] = Ratios were calculated from 3 dogs excluding baseline corrections that yielded negative values.
[c] median emulsion particle size (D50) 2.8 μm Following administration of the emulsion formulation 2, the $C_{max\ corr}$ and $AUC_{0-8\ corr}$ values for total EPA and DHA were at least 3- or 4- fold greater than those of K85EE. The corresponding values for free EPA and DHA also increased relative to K85EE. These data provide evidence of enhanced $F=AUC_{(0-8)}$ test formulation/$AUC_{(0-8)}$ reference formulation Mean $C_{max\ corr}$ and mean $AUC_{0-8\ corr}$ values were compared to K85EE oil (formula 1) data from Study A and were similarly expressed as ratios. Results are shown in Table 2:

TABLE 2

| Formulation (median emulsion particle size) | Exposure Ratios[a] | | | | | | | |
|---|---|---|---|---|---|---|---|---|
| | Total EPA | | Total DHA | | Free EPA | | Free DHA | |
| | $C_{max}$ | $AUC_{0-8}$ | $C_{max}$ | $AUC_{0-8}$ | $C_{max}$ | $AUC_{0-8}$ | $C_{max}$ | $AUC_{0-8}$ |
| 3—(130 nm) | 2.75 | 2.70 | 2.76 | 2.00 | 3.56 | 2.28 | 4.36 | 2.97 |
| 4—(150 nm) | 2.11 | 2.29 | 1.98 | 2.12 | 1.40 | 1.41 | 1.54 | 1.60 |
| 5—(1.8 μm) | 2.83 | 2.82 | 3.29 | 2.72 | 1.77 | 1.46 | 2.58 | 1.96 |
| 6—(6.3 μm) | 1.42 | 1.46 | 1.34 | 1.00 | 1.41 | 1.16 | 1.60 | 1.19 |
| 7—(130 nm) | 3.78 | 3.34 | 3.51 | 2.60 | 2.62 | 2.23 | 3.99 | 2.89 |
| 8—(12.8 μm) | 0.96 | 0.89 | 0.64 | 0.64 | 0.78 | 0.71 | 0.75 | 0.73 |

[a] = Ratios of relative exposure (test formulation/100% K85EE) for EPA and DHA (each total and free) were calculated from corrected $C_{max}$ and $AUC_{0-8}$ values ($C_{max\ corr}$ and $AUC_{0-8\ corr}$).
n = 4 dogs/group.

Following administration of the emulsion formulations 3, 4, 5 or 7 (having a median particle size of from 130 nm-1.8 μm as shown), the total $AUC_{0-8\ corr}$ values for EPA and DHA were at least 2- or 3- fold greater than those of K85EE. The corresponding values for free EPA and DHA were also increased relative to K85EE. Formulation 6 (median particle size 6.3 μm) exhibited no, or a lesser, increase in total $Cmax_{0-8\ corr}$ and $AUC_{0-8\ corr}$ values for EPA and DHA compared to K85EE. Formulation 8 (median particle size 12.8 μm) exhibited decreased exposure ($C_{max\ corr}$ and $AUC_{0-8\ corr}$ values for both total and free EPA and DHA), compared to K85EE.

Example 4

Clinical Study

A study was conducted to evaluate the relative bioavailability of EPA and DHA in plasma following oral administration of K85EE liquid emulsion and/or emulsion pre-concentrate capsules, compared to commercial K85EE (e.g. LOVAZA® capsules), and any dose-related increase in the incorporation of EPA and DHA into phospholipids following repeated dosing with emulsion.

Part A comprised single dose administration of emulsion pre-concentrate capsules or liquid emulsion equivalent to 1.68 g LOVAZA®. Part B comprised two-week, repeat dosing of selected doses of the emulsion pre-concentrate capsules.

Primary endpoints were: for Part A, free and total EPA and DHA $AUC_{(0-\infty)}$ and Cmax (corrected from baseline) following a single dose; and for Part B, $AUC_{(0-24h)}$ and $Cmax_{SS}$ for both EPA and DHA (total and free; corrected for baseline); and EPA and DHA incorporation into plasma phospholipids (absolute and % change from baseline).

More specifically, Part A was an open-label, randomized, parallel group study in healthy adult subjects to compare the relative bioavailability of a single dose of an encapsulated K85EE emulsion pre-concentrate with commercially available LOVAZA® capsules and with a liquid emulsion formulation prepared from the pre-concentrate capsules. Sixteen healthy subjects meeting eligibility criteria were randomized to each of the 3 parallel treatment groups (target at least 12 subjects completing the study). Eligible subjects checked into the clinical unit on Day −2 and had 24-hr EPA/DHA pharmacokinetic collections on Day −1 and on Day 1.

Three doses of emulsion pre-concentrate capsules were further studied in Part B. Subjects from Part A participated in Part B after at least a 3-week washout period.

Part B was a single blind, randomized, parallel group, placebo controlled study consisting of a 2-week repeat dose period with 3 dose levels of the K85EE emulsion pre-concentrate capsules, and one dose of LOVAZA®. Within each cohort, at least eight healthy subjects were randomized to an active treatment group, and at least 2 subjects were randomized to a matching placebo (1000 mg capsule containing corn oil, NF 994 mg and D-Alpha Tocopherol, USP 6 mg). Data from placebo subjects was pooled for analysis. Subjects, checked into the clinical research unit, participated in a test meal on Day −2 and had 24-hr baseline EPA/DHA profiles on Day −1 and Day 1. Subjects were released from the clinic on Day 2, and returned for daily dosing on Days 3 through 12 (with a brief outpatient visit on Day 6). Subjects checked into the clinic again on the evening of Day 12, and on Day 13 they had 24-hr EPA/DHA profiles collected. Subjects were released from the clinic on Day 14, following procedures including a test meal and triglyceride sampling.

In summary, in Part A subjects were assigned to receive a single dose of one of the treatments below:

| Treatment | Treatment Description | Dose | Number of Capsules |
|---|---|---|---|
| A | K85EE Emulsion Pre-concentrate Capsule | 1.68 g | 2 |
| B | K85EE Liquid emulsion | 1.68 g | NA |
| C | LOVAZA ® | 4 g | 4 |

Summary of Part A Dosage/Administration:

| | Product name: | | |
|---|---|---|---|
| | Emulsion Pre-concentrate Capsule | Liquid Emulsion | LOVAZA ® |
| Formulation: | K85EE Emulsion Pre-concentrate Capsule[1] | K85EE Emulsion Pre-concentrate Capsule[1] | Commercially available formulation |
| Dosage form: | Capsule | Liquid prepared from capsule | Capsule |
| Unit dose strength(s)/ Dosage level(s): | Two capsules comprising 1200 mg pre-concentrate (containing 840 mg K85EE)/capsule | Two capsules comprising 1200 mg pre-concentrate (containing 840 mg K85EE)/capsule, content dispersed in 200 mL apple juice to form an emulsion[2] | Four 1 g capsules |

-continued

| | Product name: | | |
|---|---|---|---|
| | Emulsion Pre-concentrate Capsule | Liquid Emulsion | LOVAZA ® |
| Dosing instructions: | Administered orally in the fasted state[3] with 400 mL apple juice. | Administered orally in the fasted state[3]. Capsules are opened, weighed and given with approximately 200 mL and rinsed for leftover dose with an additional 200 mL apple juice. | Administered orally in the fasted state[3] with 400 mL juice. |

[1]Formulation (9): K85EE 70 wt %, Cremophor ELP 4.5 wt %, Polysorbate 80 25.5 wt %, based on the total amount of K85EE and surfactants, and containing about 0.8-0.9 wt % water based on the total weight of the composition. Upon dispersion in water, the resulting emulsion had a median particle size 0.14 μm (140 nm), x90 0.45 μm
[2]Upon dispersion in apple juice, the resulting emulsion had a median particle size of 150 nm
[3]minimum of 10 hrs fasting In Part B, subjects were assigned to either a) one of 3 dose levels of the K85EE emulsion pre-concentrate capsules, b) LOVAZA®, or c) to placebo to match one of the 4 active treatments. Subjects were blinded as to whether they were receiving an active treatment or the corresponding placebo. The randomization ratio for active: placebo within each cohort was 4:1. Part B treatments are summarized below:

| Treatment | Treatment Description | Dose[1] | Number of Capsules |
|---|---|---|---|
| D | K85EE Emulsion Pre-concentrate Capsule | 0.84 g | 1 |
| E | K85EE Emulsion Pre-concentrate Capsule | 1.68 g | 2 |
| F | K85EE Emulsion Pre-concentrate Capsule | 3.36 g | 4 |
| G | LOVAZA ® | 4 g | 4 |
| H | Placebo for Treatment D | 0 | 1 |
| I | Placebo for Treatment E | 0 | 2 |
| J | Placebo for Treatment F | 0 | 4 |
| K | Placebo for Treatment G | 0 | 4 |

The K85EE emulsion pre-concentrate capsules and LOVAZA® were administered as capsules, once daily in the manner described for Part A, and the placebos were administered as for the corresponding active treatment. Subjects were required to fast only on PK sampling days.

The emulsion pre-concentrate formulation was as for Part A. The emulsion pre-concentrate capsules were formed by direct encapsulation of a mixture comprising the K85EE oil and surfactant into soft gelatin capsules. The K85EE and surfactant was blended and about 1 wt % water was added and mixed to form a homogeneous solution, which was encapsulated using rotary encapsulation (gel mass comprising gelatin, glycerol and water), to form capsules size 22 or 24 oblong with a nominal shell weight of 675 mg, fill weight of 1200 mg, and minimum 0.010 inch seal thickness. The capsules were dried to a hardness of at least 8.5 newtons (tumble drying in a rotary dryer for about 60 minutes followed by tunnel drying in shallow trays, generally checking hardness at least about twice daily), and cleaned with isopropyl alcohol to remove lubricant oil used during the process.

Plasma EPA and DHA concentrations were determined according to the above method.

EPA and DHA concentration in plasma phospholipids was also determined. Plasma samples are thawed and 100 μL transferred to a glass test tube. 2 mL methylene chloride, 2 mL methanol and 1 mL of distilled water are added and the tube is shaken (Multivortex, 2 min) then centrifuged (3000 rpm, 10 min) to separate the organic and aqueous layers. 200 μL of the organics is loaded onto a silica gel G thin layer chromatography plate using an Autospotter. The plate is developed with hexane:ethyl ether:acetic acid (240:60:4.5 v/v/v), and when the solvent reaches the plate midline, the plate is removed and dried (hood) for about 5 min. The plate is then placed into a tank of elemental Iodine to detect the phospholipid band (origin), removed and provided 10-15 minutes to dissipate Iodine. The bands are scraped into a reaction vial containing 250 μL BF3-methanol and 250 μL hexane. The vial is capped and heated (10 min, 100° C.). After cooling, 250 μL of water is added, the tube is capped and vortexed 30 sec and centrifuged as above to separate the layers. 50 μL of the hexane layer is transferred to a GC (gas chromatography) vial and analyzed by GC (GC2010, Shimadzu, Columbia Md., with capillary column SP2560, 100 m, Supelco, Bellefonte Pa.; 1.75 min at 180° C., ramp 5° C./min to 200° C., 1.75 min at 200° C., ramp 10° C./min to 240° C., 4.5 min at 240° C.; hydrogen carrier; or equivalent conditions).

The study results included the following.

Part A:

The following Tables 3-4 summarize some plasma AUC and Cmax data for total and free EPA and DHA, corrected for baseline, obtained for the regimens in Part A (Visit Day 1).

TABLE 3

Total EPA and DHA - Plasma AUC and Cmax (Baseline Corrected)[1]

| | Total EPA | | Total DHA | |
|---|---|---|---|---|
| Regimen | AUC(0-24) (ug•hr/mL) | Cmax (ug/mL) | AUC(0-24) (ug•hr/mL) | Cmax (ug/mL) |
| A | 278 | 26.9 | 121 | 20.3 |
| | (232, 332) | (22.3, 32.6) | (89.6, 162) | (16.4, 25.1) |
| | 34.5 | 36.8 | 60.3 | 41.6 |
| B | 440 | 41.8 | 213 | 35.5 |
| | (377, 514) | (34.3, 50.9) | (151, 301) | (28.2, 44.8) |
| | 29.8 | 38.5 | 72.2 | 45.5 |
| C | 54.3 | 4.77 | 22.2 | 6.38 |
| | (30.5, 96.7) | (2.79, 8.15) | (5.68, 86.4) | (4.22, 9.64) |
| | 130.7 | 132 | 363 | 90.9 |

[1]Data reported as Geometric mean (95% CI) CVb %. Unless otherwise stated, N = 16 for each regimen.
Regimen Key:
A - Emulsion Capsule 1.68 g
B - Liquid Emulsion 1.68 g
C - LOVAZA 4 g

TABLE 4

Free EPA and DHA - Plasma AUC and Cmax (Baseline Corrected)[1]

| | Free EPA | | Free DHA | |
|---|---|---|---|---|
| Regimen | AUC(0-24) (ug•hr/mL) | Cmax (ug/mL) | AUC(0-24) (ug•hr/mL) | Cmax (ug/mL) |
| A | 1.26 | 0.178 | 2.72 | 0.502 |
| | (0.951, 1.68) | (0.148, 0.215) | (2.28, 3.25) | (0.430, 0.587) |
| | 52.4[2] | 33.6[2] | 33.9 | 30.0 |
| B | 2.10 | 0.305 | 4.97 | 0.931 |
| | (1.77, 2.49) | (0.243, 0.383) | (4.36, 5.67) | (0.750, 1.16) |
| | 29.0[3] | 39.2[3] | 25.1 | 42.3 |

TABLE 4-continued

Free EPA and DHA - Plasma AUC and Cmax (Baseline Corrected)[1]

| Regimen | Free EPA | | Free DHA | |
|---|---|---|---|---|
| | AUC(0-24) (ug·hr/mL) | Cmax (ug/mL) | AUC(0-24) (ug·hr/mL) | Cmax (ug/mL) |
| C | 0.275 (0.101, 0.748) 211 | 0.042 (0.026, 0.066) 106 | 0.528 (0.212, 1.31) 230 | 0.282 (0.211, 0.377) 59.0 |

[1]Geometric mean (95% CI) CVb %. Unless otherwise stated, N = 16 for each regimen.
[2]n = 14.
[3]n = 13.
Regimen Key:
A - Emulsion Capsule 1.68 g
B - Liquid Emulsion 1.68 g
C - LOVAZA 4 g Mean Cmax and AUC values for free and total EPA and DHA were several-fold higher for the subjects dosed with the emulsion capsules and the liquid emulsion when compared to the LOVAZA treatment. These PK parameters were approximately 2-fold higher for the subjects dosed with the liquid emulsion relative to those dosed with the emulsion capsule. Moderate to high intersubject variability was observed for the Cmax and AUC estimates. Variability between subjects was less for subjects dosed with the emulsion capsules or the liquid emulsion, compared to the LOVAZA treatment. Therefore, the compositions of the invention may provide for better predictability in dosing/dose-setting.

Statistical analyses included comparison of the dose-normalized, baseline-corrected Cmax and AUC(0-24) values of the emulsion capsules, liquid emulsion and LOVAZA regimens from Part A, and included results shown in Table 5.

TABLE 5

Point Estimates and 90% CI's for Comparison of Dose-normalized Baseline-corrected Pharmacokinetic (PK) Parameters on Day 1 (following single dosing of formulations in Part A)

| Analyte | PK Parameter[1] | Comparison[2] | Geometric LS Mean[3] ($\times 10^3$) | | Ratio | 90% CI | CVb (%) |
|---|---|---|---|---|---|---|---|
| | | | Test | Reference | | | |
| Total EPA | AUC(0-24 h) (ug·hr/mL) | A:C | 401.35 | 28.36 | 14.15 | 9.78, 20.49* | 64.26 |
| | | B:C | 601.45 | 28.36 | 21.21 | 14.75, 30.50* | |
| | | A:B | 401.35 | 601.45 | 0.67 | 0.47, 0.95 | |
| | Cmax (ug/mL) | A:C | 39.41 | 2.46 | 16.02 | 10.94, 23.46* | 69.12 |
| | | B:C | 57.32 | 2.46 | 23.29 | 16.04, 33.84* | |
| | | A:B | 39.41 | 57.32 | 0.69 | 0.47, 1.00 | |
| Total DHA | AUC(0-24 h) (ug·hr/mL) | A:C | 183.37 | 17.53 | 10.46 | 5.68, 19.26* | 97.18 |
| | | B:C | 383.27 | 17.53 | 21.86 | 12.03, 39.72* | |
| | | A:B | 183.37 | 383.27 | 0.48 | 0.29, 0.79* | |
| | Cmax (ug/mL) | A:C | 34.57 | 4.49 | 7.70 | 5.42, 10.96* | 61.81 |
| | | B:C | 60.40 | 4.49 | 13.46 | 9.58, 18.91* | |
| | | A:B | 34.57 | 60.40 | 0.57 | 0.41, 0.81 | |
| Free EPA | AUC(0-24 h) (ug·hr/mL) | A:C | 1.75 | 0.14 | 12.25 | 7.34, 20.46* | 80.28 |
| | | B:C | 2.97 | 0.14 | 20.85 | 12.36, 35.17* | |
| | | A:B | 1.75 | 2.97 | 0.59 | 0.37, 0.93 | |
| | Cmax (ug/mL) | A:C | 0.24 | 0.02 | 10.74 | 7.43, 15.54* | 65.62 |
| | | B:C | 0.42 | 0.02 | 18.61 | 12.76, 27.13* | |
| | | A:B | 0.24 | 0.42 | 0.58 | 0.39, 0.85 | |
| Free DHA | AUC(0-24 h) (ug·hr/mL) | A:C | 4.66 | 0.37 | 12.56 | 7.73, 20.43* | 84.12 |
| | | B:C | 8.42 | 0.37 | 22.68 | 13.99, 36.75* | |
| | | A:B | 4.66 | 8.42 | 0.55 | 0.36, 0.86 | |
| | Cmax (ug/mL) | A:C | 0.88 | 0.19 | 4.55 | 3.50, 5.91* | 44.37 |
| | | B:C | 1.59 | 0.19 | 8.24 | 6.38, 10.63* | |
| | | A:B | 0.88 | 1.59 | 0.55 | 0.43, 0.71* | |

A = 1.68 g Emulsion Capsule. (Dose: EPA 726 mg; DHA 588 mg)
B = 1.68 g Liquid Emulsion. (Dose: EPA 726 mg; DHA 58 8mg)
C = 4 g LOVAZA. (Dose: EPA 1832 mg; DHA 1416 mg)
* = comparison was statistically significant at the 10% level.
[1]Dose normalized and baseline corrected pharmacokinetic parameters.
[2]Analysed using ANCOVA, fitting fixed effects for treatment, and including baseline value as a covariate.
[3]$\times 10^3$ to keep precision.

Free and total EPA/DHA Cmax and AUC(0-24) values were significantly higher in both the emulsion capsule and liquid emulsion relative to LOVAZA 4 g. Compared to LOVAZA 4 g, free and total EPA and DHA baseline-corrected AUC(0-24) values were 10 to 14-fold higher for the emulsion capsule and 21 to 23-fold higher for the liquid emulsion. The 90% CIs associated with free and total EPA and DHA baseline-corrected AUC(0-24) values were completely outside the 0.8 to 1.25 interval.

Free and total EPA/DHA Cmax and AUC(0-24) values were significantly higher for the liquid emulsion formulation than the emulsion capsule. Compared to the emulsion capsule, free and total EPA and DHA baseline-corrected AUC (0-24) values were 33 to 52% higher for the liquid emulsion.

Without intending to be bound or limited by theory, it is believed that the liquid emulsion is less subject to variations in digestive activity, including GI tract conditions and transit, and therefore exhibits a higher exposure relative to the emulsion pre-concentrate capsule. This higher exposure might approximate the maximum exposure which could potentially be achieved with a corresponding emulsion capsule. The capsule form is preferred, for example for providing protection from degradation, as well as ease of use and patient compliance.

Part B:

Tables 6 and 7 summarize some plasma AUC and Cmax data for total and free EPA/DHA, corrected for baseline, obtained for the regimens in Part B.

TABLE 6

Plasma Total EPA and DHA Pharmacokinetic Parameters: Part B (0-24 hours), Baseline-Corrected[1]

| | | | Total EPA | | | Total DHA | |
|---|---|---|---|---|---|---|---|
| Visit | Regimen | n | AUC(0-24) (ug · hr/mL) | Cmax (ug/mL) | n | AUC(0-24) (ug · hr/mL) | Cmax (ug/mL) |
| Day 1 | D | 11 | 161 (127, 204) 36.8 | 13.7 (10.3, 18.2) 44.5 | 11 | 35.8 (16.7, 76.8) 163 | 10.8 (6.95, 16.7) 72.6 |
| | E | 8 | 261 (189, 361) 40.3 | 26.6 (18.8, 37.6) 43.2 | 8 | 144 (87.4, 236) 57.9 | 20.5 (12.6, 33.4) 63.7 |
| | F | 10 | 519 (351, 769) 59.3 | 53.5 (36.6, 78.4) 57.3 | 10 | 219 (138, 349) 72.2 | 39.1 (26.3, 58.2) 60.0 |
| | G | 9 | 48.5 (16.5, 143) 208 | 4.23 (2.21, 8.10) 102 | 9 | 15.2 (2.22, 104) 182 | 3.37 (1.91, 5.93) 84.7 |
| | P | 9 | 24.7 (17.2, 35.4) 45.2 | 2.17 (1.17, 4.02) 95.3 | 9 | 16.5 (2.19, 124) 200 | 2.70 (1.38, 5.29) 107 |
| Day 13 | D | 10 | 368 (258, 524) 52.6 | 22.7 (15.3, 33.6) 59.4 | 10 | 368 (244, 557) 62.9 | 25.9 (16.5, 40.8) 70.3 |
| | E | 8 | 649 (523, 805) 26.3 | 43.0 (33.9, 54.5) 29.0 | 8 | 675 (522, 872) 31.4 | 44.5 (33.8, 58.8) 34.1 |
| | F | 10 | 1190 (936, 1520) 34.8 | 82.3 (63.8, 106) 36.8 | 10 | 1040 (772, 1390) 42.9 | 74.5 (56.1, 98.9) 41.2 |
| | G | 9 | 372 (193, 718) 104 | 21.2 (11.7, 38.4) 90.3 | 9 | 454 (269, 765) 76.6 | 27.9 (18.4, 42.3) 58.3 |
| | P | 9 | 13.4 (5.98, 29.9) 72.3 | 1.29 (0.608, 2.75) 97.5 | 9 | 53.6 (4.92, 584) 27.1 | 2.96 (0.265, 33.1) 300 |

[1]Geometric mean (95% CI) CVb %.
Regimen key:
D = Emulsion Capsule 0.84 g (N = 11).
E = Emulsion Capsule 1.68 g (N = 8).
F = Emulsion Capsule 3.36 g (N = 10).
G = LOVAZA 4 g (N = 9).
P = Placebo (Pooled) (N = 9).

TABLE 7

Plasma Free EPA and DHA Pharmacokinetic Parameters: Part B (0-24 hours), Baseline-Corrected[1]

| | | | Free EPA | | | Free DHA | |
|---|---|---|---|---|---|---|---|
| Visit | Regimen | n | AUC(0-24) (ug · hr/mL) | Cmax (ug/mL) | n | AUC(0-24) (ug · hr/mL) | Cmax (ug/mL) |
| Day 1 | D | 10 | 0.673 (0.446, 1.02) 40.9 | 0.053 (0.032, 0.089) 82.6 | 11 | 0.648 (0.288, 1.46) 182 | 0.324 (0.268, 0.392) 29.0 |

TABLE 7-continued

Plasma Free EPA and DHA Pharmacokinetic Parameters: Part B (0-24 hours), Baseline-Corrected[1]

| | | | Free EPA | | | Free DHA | |
|---|---|---|---|---|---|---|---|
| Visit | Regimen | n | AUC(0-24) (ug · hr/mL) | Cmax (ug/mL) | n | AUC(0-24) (ug · hr/mL) | Cmax (ug/mL) |
| | E | 7 | 1.21 (0.736, 1.97) 57.3 | 0.155 (0.103, 0.233) 46.2 | 8 | 2.70 (1.64, 4.43) 64.9 | 0.443 (0.306, 0.643) 46.8 |
| | F | 10 | 2.72 (2.22, 3.33) 28.7 | 0.356 (0.267, 0.476) 42.1 | 10 | 4.36 (3.57, 5.33) 28.7 | 0.817 (0.585, 1.14) 49.4 |
| | G | 7 | 0.515 (0.179, 1.48) 103 | 0.032 (0.012, 0.088) 154 | 9 | 0.615 (0.219, 1.73) 128 | 0.201 (0.139, 0.291) 50.8 |
| | P | 8 | 0.442 (0.128, 1.53) 174 | 0.047 (0.030, 0.076) 61.7 | 9 | 0.300 (0.084, 1.08) 239 | 0.303 (0.232, 0.397) 36.1 |
| Day 13 | D | 9 | 1.02 (0.528, 1.96) 92.3 | 0.102 (0.070, 0.150) 53.2 | 10 | 2.48 (1.94, 3.16) 35.1 | 0.455 (0.354, 0.585) 36.2 |
| | E | 7 | 2.58 (1.90, 3.49) 33.9 | 0.228 (0.172, 0.301) 30.9 | 8 | 5.25 (3.93, 7.01) 35.7 | 0.653 (0.530, 0.806) 25.5 |
| | F | 10 | 6.04 (4.88, 7.47) 30.4 | 0.608 (0.494, 0.748) 29.6 | 10 | 9.69 (8.09, 11.6) 25.7 | 1.38 (1.18, 1.61) 22.3 |
| | G | 8 | 1.62 (0.703, 3.74) 131 | 0.134 (0.063, 0.282) 110 | 9 | 3.28 (1.70, 6.31) 103 | 0.529 (0.327, 0.856) 69.3 |
| | P | 8 | 0.509 (0.138, 1.88) 142 | 0.034 (0.019, 0.061) 68.8 | 9 | −0.166[2] (−0.736, 0.403) 452 | 0.228 (0.147, 0.354) 62.4 |

[1]Geometric mean (95% CI) CVb %.
[2]Arithmetic mean (95% CI) CVb % presented as limited positive data was observed when AUC was log transformed.
Regimen key:
D = Emulsion Capsule 0.84 g (N = 11).
E = Emulsion Capsule 1.68 g (N = 8).
F = Emulsion Capsule 3.36 g (N = 10).)
G = LOVAZA 4 g (N = 9).
P = Placebo (Pooled) (N = 9).

Free and total EPA/DHA Cmax and AUC(0-24) values were generally much lower for the pooled placebo group when compared to the exposure from the subjects dosed with the 3 dose levels of emulsions capsules or LOVAZA. Cmax and AUC(0-24) values increased with the increase in K85EE emulsion capsule dose from 0.84 g to 3.36 g for free and total EPA/DHA. Free and total EPA/DHA Cmax and AUC(0-24) values were higher on Day 13 than on Day 1, indicating accumulation of free and total EPA/DHA following repeat dosing of both the emulsion capsules and LOVAZA. Moderate to high intersubject variability was observed with free and total EPA and DHA Cmax and AUC estimates.

Parametric analysis for assessment of accumulation of free and total EPA/DHA following repeat dosing was conducted for each of the Part B regimens and included the results shown in Table 8.

TABLE 8

Parametric Analysis Result for Assessment of Accumulation of Free and Total EPA/DHA following Repeat Dosing of Formulations in Part B

| | | | | Geometric LS Mean | | | | CVw | CVb |
|---|---|---|---|---|---|---|---|---|---|
| Analyte | Parameter[1] | Comparison | Regimen | Test | Ref. | Ratio | 90% CI | (%) | (%) |
| Total EPA | AUC(0-24 h) (ug · hr/mL) | Day13:Day1 | D | 570.78 | 353.88 | 1.61 | 1.36, 1.91*/** | 23.24 | 28.36 |
| | | | E | 796.01 | 447.59 | 1.78 | 1.47, 2.16*/** | | |
| | | | F | 1433.62 | 736.47 | 1.95 | 1.64, 2.31*/** | | |
| | | | G | 611.34 | 251.67 | 2.43 | 2.03, 2.91*/** | | |
| | Cmax (ug/mL) | Day13:Day1 | D | 30.87 | 21.90 | 1.41 | 1.19, 1.67* | 22.96 | 33.37 |
| | | | E | 47.81 | 33.20 | 1.44 | 1.19, 1.74* | | |
| | | | F | 93.55 | 63.98 | 1.46 | 1.23, 1.73* | | |
| | | | G | 30.84 | 12.86 | 2.40 | 2.00, 2.87*/** | | |
| Total DHA | AUC(0-24 h) (ug · hr/mL) | Day13:Day1 | D | 1208.08 | 875.80 | 1.38 | 1.27, 1.50*/** | 11.03 | 14.26 |
| | | | E | 1486.63 | 967.60 | 1.54 | 1.40, 1.69*/** | | |
| | | | F | 1910.92 | 1077.14 | 1.77 | 1.63, 1.93*/** | | |
| | | | G | 1356.51 | 810.21 | 1.67 | 1.53, 1.83*/** | | |

TABLE 8-continued

Parametric Analysis Result for Assessment of Accumulation of Free and
Total EPA/DHA following Repeat Dosing of Formulations in Part B

| Analyte | Parameter[1] | Comparison | Regimen | Geometric LS Mean Test | Ref. | Ratio | 90% CI | CVw (%) | CVb (%) |
|---|---|---|---|---|---|---|---|---|---|
| | Cmax (ug/mL) | Day13:Day1 | D | 60.66 | 45.92 | 1.32 | 1.21, 1.44*/** | 11.40 | 19.74 |
| | | | E | 77.67 | 56.18 | 1.38 | 1.26, 1.52*/** | | |
| | | | F | 111.47 | 76.86 | 1.45 | 1.33, 1.58*/** | | |
| | | | G | 65.37 | 38.29 | 1.71 | 1.56, 1.87*/** | | |
| Free EPA | AUC(0-24 h) (ug · hr/mL) | Day13:Day1 | D | 2.62 | 1.69 | 1.55 | 1.30, 184** | 22.36 | 31.04 |
| | | | E | 3.99 | 2.73 | 1.46 | 1.20, 1.79* | | |
| | | | F | 7.31 | 3.93 | 1.86 | 1.57, 2.20*/** | | |
| | | | G | 3.22 | 1.66 | 1.94 | 1.59, 2.36*/** | | |
| | Cmax (ug/mL) | Day13:Day1 | D | 0.18 | 0.13 | 1.40 | 1.14, 1.71* | 26.46 | 32.70 |
| | | | E | 0.29 | 0.22 | 1.30 | 1.03, 1.64* | | |
| | | | F | 0.66 | 0.41 | 1.62 | 1.33, 1.97* | | |
| | | | G | 0.20 | 0.09 | 2.10 | 1.67, 2.64*/** | | |
| Free DHA | AUC(0-24 h) (ug · hr/mL) | Day13:Day1 | D | 7.90 | 6.28 | 1.26 | 1.12, 1.41* | 15.17 | 17.63 |
| | | | E | 10.89 | 8.32 | 1.31 | 1.15, 1.49* | | |
| | | | F | 15.34 | 9.77 | 1.57 | 1.40, 1.76*/** | | |
| | | | G | 9.40 | 5.61 | 1.67 | 1.49, 1.89*/** | | |
| | Cmax (ug/mL) | Day13:Day1 | D | 0.68 | 0.55 | 1.24 | 1.03, 1.50* | 26.29 | 27.22 |
| | | | E | 0.89 | 0.68 | 1.32 | 1.06, 1.64* | | |
| | | | F | 1.62 | 1.06 | 1.52 | 1.26, 1.85* | | |
| | | | G | 0.79 | 0.43 | 1.85 | 1.50, 2.27*/** | | |

D = Emulsion Capsule 0.84 g. (Dose: EPA 363 mg; DNA 294 mg)
E = Emulsion Capsule 1.68 g. (Dose: EPA 726 mg; DNA 588 mg)
F = Emulsion Capsule 3.36 g. (Dose: EPA 1452 mg; DNA 1176 mg)
G = LOVAZA 4 g. (Dose: EPA 1832 mg; DNA 1416 mg)
* = comparison was statistically significant at the 10% level.
** = comparison was statistically significant at p < 0.0001.
[1]0-24 h pharmacokinetic parameters
[2]Analysed using ANCOVA, fitting fixed effects for treatment, day, treatment by day, and including baseline value as a covariate.

Free and total EPA and DHA AUC(0-24) values increased significantly on Day 13 compared to Day 1 for both the emulsion capsules and LOVAZA (4g). Compared to Day 1, free and total EPA and DHA AUC(0-24) values on Day 13 increased by 1.26 to 1.95-fold for the emulsion capsules and by 1.67 to 2.43-fold for LOVAZA 4 g. The 90% CIs associated with free and total EPA and DHA AUC(0-24) values were generally outside the 0.8 to 1.25 interval for the Day 13:Day 1 comparison. The results indicate significant accumulation of free and total EPA and DHA after repeat dosing of the emulsion capsules (0.84 to 3.36 g K85EE) and LOVAZA 4 g for 13 days.

Dose proportionality of EPA and DHA (total and free) after repeat dosing of the emulsion formulations was assessed and included the results shown in Table 9.

TABLE 9

Analysis results for Assessment of Dose Proportionality
for Free and Total EPA/DHA following
Repeat Dosing of Emulsion Formulations in Part B

| Analyte | Parameter[1] | Slope[2] | 90% CI | CVb (%) |
|---|---|---|---|---|
| Total EPA | AUC(0-24 h) (ug hr/mL) | 0.85 | 0.64, 1.06 | 39.10 |
| | Cmax (ug/mL) | 0.93 | 0.70, 1.16 | 43.10 |
| Total DHA | AUC(0-24 h) (ug hr/mL) | 0.75 | 0.50, 0.99* | 47.17 |
| | Cmax (ug/mL) | 0.76 | 0.50, 1.02 | 49.96 |
| Free EPA | AUC(0-24 h) (ug hr/mL) | 1.28 | 0.99, 1.58 | 53.37 |
| | Cmax (ug/mL) | 1.29 | 1.08, 1.50* | 38.63 |
| Free DHA | AUC(0-24 h) (ug hr/mL) | 0.98 | 0.81, 1.15 | 31.66 |
| | Cmax (ug/mL) | 0.80 | 0.64, 0.96* | 29.67 |

*Significant at 10% level.
[1]0-24 h Pharmacokinetic parameters.
[2]Analyzed using Power Model.

There were no major deviations from dose proportionality for total EPA and free DHA. The exposure of free EPA after repeat dosing was greater than proportional to dose, and the exposure of total DHA after repeat dosing was less than proportional to dose.

The percent of incorporation of EPA into plasma phospholipids over a 24-hour measured period is presented in Table 10 for AUC over 24 hours. Similar patterns were observed for Cmax.

TABLE 10

EPA and DHA Incorporation into Phospholipids - Parameters

| Regimen | | N | Geometric Mean AUC (0-24 hr*%) (95% CI) | | |
|---|---|---|---|---|---|
| | | | Day −1 | Day 1 | Day 13 |
| EPA % | D | 11 | 6.97 (5.75, 8.46) | 15.61 (12.0, 20.3) | 27.7 (24.3, 31.6) |
| | E | 8 | 8.54 (6.12, 11.9) | 18.4 (14.7, 23.0) | 44.3 (37.2, 52.9) |
| | F | 10 | 7.30 (5.86, 9.09) | 28.3 (24.0, 33.4) | 67.2 (57.9, 77.9) |
| | G | 9 | 8.60 (6.86, 10.8) | 11.5 (9.06, 14.6) | 34.5 (24.7, 48.3) |
| | P | 9 | 7.56 (5.48, 10.4) | 10.2 (8.52, 12.2) | 10.9 (8.79, 13.4) |
| DHA % | D | 11 | 50.0 (44.6, 56.1) | 54.3 (47.8, 61.8) | 74.5 (67.8, 81.9) |
| | E | 8 | 51.8 (40.6, 65.9) | 55.1 (42.0, 72.2) | 98.9 (82.2, 119) |
| | F | 10 | 48.8 (40.2, 59.3) | 59.3 (50.1, 70.2) | 110 (99.4, 123) |
| | G | 9 | 49.5 (42.4, 57.7) | 51.9 (45.5, 59.1) | 89.3 (77.3, 103) |
| | P | 9 | 51.3 (46.4, 56.7) | 54.0 (48.2, 60.5) | 53.0 (50.1, 56.0) |

D: Emulsion Capsule 0.84 g
E: Emulsion Capsule 1.68 g
F: Emulsion Capsule 3.36 g
G: Lovaza 4 g
P: Placebo (pooled)

Table 11 reflects percent change from baseline in the average exposure (Cmean calculated from the AUC[0-24 h] divided by 24), Day 13:

TABLE 11

| Treatment | Cmean, % EPA | Cmean, % DHA |
|---|---|---|
| D | 278 | 46 |
| E | 415 | 89 |
| F | 810 | 118 |
| G | 282 | 78 |
| P | 37 | 11 |

Dose proportionality of Cmean was assessed with point estimates (% CI) of 0.77 (0.55, 0.99) for EPA and 0.67 (0.41, 0.94) for DHA. Parametric analysis of the emulsion treatment arms compared to LOVAZA as the reference indicate that EPA and DHA incorporation (Cmean) was significantly higher for Treatment F and the DHA incorporation for Treatment D was significantly lower.

Incorporation of EPA and DHA in plasma phospholipids at pre-dose on Days −1, 1, 6 and 13 was assessed. As shown in Table 12, EPA and DHA were increased in all active treatment groups over the dosing period, EPA to a greater degree:

TABLE 12

| | DHA - % increase Day 13 (pre-dose) | EPA - % increase Day 13 (pre-dose) |
|---|---|---|
| D | 33 | 234 |
| E | 88 | 427 |
| F | 92 | 790 |
| G | 62 | 366 |

EPA and DHA incorporation into plasma phospholipids showed dose-related increases, as well as increases at Day 13 for the active treatment groups. The incorporation profile for LOVAZA 4 g was in-between that observed for the 1 and 2-capsule emulsion doses. The increase from baseline on Day 13 for the 24-hour AUC was greatest with the 4-capsule emulsion dose (~8-fold for EPA and ~2-fold for DHA); and was about twice that observed for LOVAZA 4g for EPA. The incorporation measured pre-dose on Days −1, 1, 6 and 13 showed a similar dose-related increase. Following repeat dosing, incorporation of EPA and DHA into phospholipids increased over baseline in all active treatment groups; the increase was dose-dependent for EPA with an 8-fold increase observed for the Emulsion 4-capsule dose compared to a 4-fold increase for LOVAZA 4 g. The incorporation of DHA was also increased, although to a lesser degree.

In addition, it was found that food affected the exposure of EPA following dosing with 4 g LOVAZA, but not with the emulsion pre-concentrate capsules. Significant increases in AUC(0-8) values were observed for free and total EPA when 4 g LOVAZA was dosed with a high-fat meal compared to the fasted state (Table 13). No food effect was observed for free and total EPA AUC(0-8) values when the emulsion pre-concentrate capsules were dosed with a high-fat meal compared to the fasted state. While not intending to be bound or limited by theory, it is believed that the LOVAZA 4 g formulation benefited from the emulsifying action of bile salts during digestion of food. In contrast, the emulsion pre-concentrate, already supplied as an emulsifiable dosage form, did not appear to benefit from or require further emulsification by bile salts for absorption.

TABLE 13

| Treatment | Ratio total EPA AUC(0-8) Fed/Fasted | Lower 90% CI | Upper 90% CI |
|---|---|---|---|
| LOVAZA | 2.11 | 1.64 | 2.71 |
| LEM-1 | 1.2 | 0.95 | 1.53 |
| LEM-2 | 1.2 | 0.92 | 1.57 |
| LEM-4 | 1.02 | 0.81 | 1.3 |

The above clinical study shows that the emulsion pre-concentrate composition provided substantive increases in EPA and DHA exposure as well as EPA and DHA incorporation into phospholipids, compared to the non-emulsified LOVAZA product. This increased bioavailability may provide increased efficacy, e.g. increased triglyceride lowering, compared to the non-emulsified LOVAZA product in subjects in need of treatment. Thus, an emulsion pre-concentrate capsule of the invention may allow for lower doses and/or fewer dosage units for the same or similar efficacy as the corresponding non-emulsified omega-3 fatty acid oil. Accordingly, less omega-3 fatty acid oil may be needed to achieve efficacy, which in turn potentially reduces environmental impacts, exposure to undesirable components of the oil, side effects, caloric intake and costs of therapy.

All publications, including but not limited to patents and patent applications, cited in this specification are herein incorporated by reference as if each individual publication were specifically and individually indicated to be incorporated by reference herein as though fully set forth.

What is claimed:

1. An oral dosage form comprising an emulsion pre-concentrate composition,
   wherein the emulsion preconcentrate composition comprises: from about 66 to about 88 wt % of an omega-3 fatty acid oil; and from about 10 to about 30 wt % of a surfactant comprising PEG 35 castor oil and polysorbate 80; based on the total weight of the omega-3 fatty acid oil and the surfactant in the composition;
   wherein the omega-3 fatty acid oil is the only active ingredient in the composition.

2. The oral dosage form of claim 1, wherein the omega-3 fatty acid oil comprises an omega-3 fatty acid selected from a) an omega-3 polyunsaturated free fatty acid; b) an ester of a polyunsaturated free fatty acid with glycerol; c) an ester of a polyunsaturated free fatty acid and a primary, secondary or tertiary alcohol; and d) a mixture thereof.

3. The oral dosage form of claim 1, wherein the omega-3 fatty acid oil comprises at least 40% by weight of one or more omega-3 fatty acids.

4. The oral dosage form of claim 1, wherein the omega-3 fatty acid oil comprises at least 50% by weight of ethyl ester of EPA and ethyl ester of DHA.

5. The oral dosage form of claim 1, wherein the omega-3 fatty acid oil comprises from about 5 to about 100% by weight of ethyl ester of EPA.

6. An oral dosage form comprising an emulsion pre-concentration composition,
   wherein the emulsion pre-concentrate composition comprises: from about 60 to about 70 wt % of omega-3 fatty acid oil; and from about 30 to about 40 wt % of a surfactant comprising polysorbate 80; based on the total weight of the omega-3 fatty acid oil and the surfactant in the composition;
   wherein the omega-3 fatty acid oil is the only active ingredient in the composition.

7. The oral dosage form of claim 6, wherein the omega-3 fatty acid oil comprises an omega-3 fatty acid selected from a) an omega-3 polyunsaturated free fatty acid; b) an ester of a polyunsaturated free fatty acid with glycerol; c) an ester of a polyunsaturated free fatty acid and a primary, secondary or tertiary alcohol; and d) a mixture thereof.

8. The oral dosage form of claim 6, wherein the omega-3 fatty acid oil comprises at least 40% by weight of one or more omega-3 fatty acids.

9. The oral dosage form of claim 6, wherein the omega-3 fatty acid oil comprises at least 50% by weight of ethyl ester of EPA and ethyl ester of DHA.

10. The oral dosage form of claim 6, wherein the omega-3 fatty acid oil comprises from about 5 to about 100% by weight of ethyl ester of EPA.

11. An oral dosage form comprising an emulsion pre-concentrate composition,
   wherein the emulsion pre-concentration composition comprises: from about 60 to about 77 wt % of omega-3 fatty acid oil; and from about 20 to about 40 wt % of a surfactant comprising PEG 35 castor oil; based on the total weight of the omega-3 fatty acid oil and the surfactant in the composition;
   wherein the omega-3 fatty acid oil is the only active ingredient in the composition.

12. The oral dosage form of claim 11, wherein the omega-3 fatty acid oil comprises an omega-3 fatty acid selected from a) an omega-3 polyunsaturated free fatty acid; b) an ester of a polyunsaturated free fatty acid with glycerol; c) an ester of a polyunsaturated free fatty acid and a primary, secondary or tertiary alcohol; and d) a mixture thereof.

13. The oral dosage form of claim 11, wherein the omega-3 fatty acid oil comprises at least 40% by weight of one or more omega-3 fatty acids.

14. The oral dosage form of claim 11, wherein the omega-3 fatty acid oil comprises at least 50% by weight of ethyl ester of EPA and ethyl ester of DHA.

15. The oral dosage form of claim 11, wherein the omega-3 fatty acid oil comprises from about 5 to about 100% by weight of ethyl ester of EPA.

\* \* \* \* \*